US009199983B2

(12) United States Patent
Cai et al.

(10) Patent No.: US 9,199,983 B2
(45) Date of Patent: Dec. 1, 2015

(54) 3-ARYL-6-ARYL-[1,2,4]TRIAZOLO[4,3-α]PYRIDINES AS INHIBITORS OF CELL PROLIFERATION AND THE USE THEREOF

(76) Inventors: Suixiong Cai, Jiangsu (CN); Ye Edward Tian, Jiangsu (CN); Haijun Dong, Shanghai (CN); Lei Chen, Jiangsu (CN); Zenghui Yu, Jiangsu (CN); Feng Yin, Jiangsu (CN); Sheng Bi, Jiangsu (CN); Lijun Liu, Jiangsu (CN); Lizhen Wu, Jiangsu (CN)

( * ) Notice: Subject to any disclaimer, the term of this patent is extended or adjusted under 35 U.S.C. 154(b) by 385 days.

(21) Appl. No.: 13/885,896

(22) PCT Filed: Nov. 16, 2011

(86) PCT No.: PCT/CN2011/082264
§ 371 (c)(1),
(2), (4) Date: Jul. 10, 2013

(87) PCT Pub. No.: WO2012/065546
PCT Pub. Date: May 24, 2012

(65) Prior Publication Data
US 2013/0280245 A1 Oct. 24, 2013

(30) Foreign Application Priority Data
Nov. 16, 2010 (WO) ................ PCT/CN2010/078761

(51) Int. Cl.
C07D 401/14 (2006.01)
A61K 31/437 (2006.01)
C07D 471/04 (2006.01)
A61K 31/444 (2006.01)
A61K 31/506 (2006.01)
A61K 45/06 (2006.01)
A61N 5/10 (2006.01)

(52) U.S. Cl.
CPC ............ *C07D 471/04* (2013.01); *A61K 31/437* (2013.01); *A61K 31/444* (2013.01); *A61K 31/506* (2013.01); *A61K 45/06* (2013.01); *A61N 5/10* (2013.01)

(58) Field of Classification Search
CPC ............................. C07D 401/14; A61K 31/437
USPC .................................. 546/119, 121; 514/303
See application file for complete search history.

(56) References Cited

U.S. PATENT DOCUMENTS

| 8,283,465 | B2 * | 10/2012 | Mitani et al. .................... 540/1 |
| 8,952,034 | B2 * | 2/2015 | Corkey et al. ................. 514/303 |
| 2005/0113283 | A1 * | 5/2005 | Solow-Cordero et al. ........ 514/1 |
| 2011/0021521 | A1 | 1/2011 | Corkey et al. |

FOREIGN PATENT DOCUMENTS

| WO | WO 2006/138657 A1 | 12/2006 |
| WO | WO 2008/063287 A2 | 5/2008 |
| WO | WO 2010/022076 A1 | 2/2010 |

OTHER PUBLICATIONS

International Search Report for International Patent Appl. No. PCT/CN2011/082264, The State Intellectual Property Office, People's Republic of China, mailed Mar. 8, 2012.

* cited by examiner

*Primary Examiner* — Niloofar Rahmani
(74) *Attorney, Agent, or Firm* — Sterne, Kessler, Goldstein & Fox P.L.L.C.

(57) ABSTRACT

Disclosed are 3-aryl-6-aryl-[1,2,4]triazolo[4,3-a]pyridines thereof, represented by the Formula (I) wherein $Ar_1$, $Ar_2$, $R_1$-$R_3$ are defined herein. Compounds having Formula (I) are inhibitors of cell proliferation. Therefore, compounds of the invention may be used to treat clinical conditions in which uncontrolled growth and spread of abnormal cells occurs.

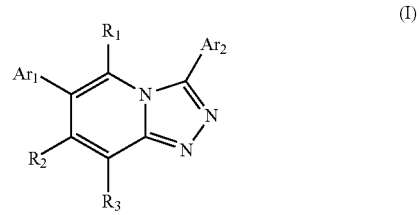

(I)

19 Claims, No Drawings

3-ARYL-6-ARYL-[1,2,4]TRIAZOLO[4,3-α]PYRIDINES AS INHIBITORS OF CELL PROLIFERATION AND THE USE THEREOF

BACKGROUND OF THE INVENTION

1. Field of the Invention

This invention is in the field of medicinal chemistry. In particular, the invention relates to 3-aryl-6-aryl-[1,2,4]triazolo[4,3-a]pyridines, and the use of these compounds as therapeutically effective anticancer agents.

2. Related Art

One of the hallmarks of cancer is the uncontrolled cell proliferation. Therefore, the discovery and development of antiproliferative agents which are cytotoxic to cancer cells and inhibit cancer cell growth can lead to effective treatment for cancer. Many novel chemotherapeutic agents have been discovered and developed in the past 50 years, including paclitaxel and docetaxel, doxorubicin and epirubicin, topotecan and irinotecan, cisplatin and carboplatin, as well as vincristine and vinblastine, and these cytotoxic drugs have been widely used for the treatment of both leukemia and solid tumors. More recently, significant successes have been made with targeted therapies, such as the successful development of BCR-ABL tyrosine kinase inhibitor imatinib for the treatment of chronic myeloid leukemia. However, cancer is a complex, aggressive and lethal disease. It remains a great challenge to find more effective anticancer drugs.

The mechanism of action of many current anticancer drugs frequently involves an attack at specific phases of the cell cycle to cause cell cycle arrest. In brief, the cell cycle refers to the stages through which cells progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as vincristine, vinblastine, and paclitaxel are M phase specific.

It has been known that many cancer chemotherapeutic drugs can trigger cancer cells to undergo apoptosis. The mechanism of apoptosis involves a cascade of initiator and effector caspases that are activated sequentially. Caspases are a family of cysteine proteases that require aspartic acid residues at the $P_1$ position of substrates for cleavage. Among these caspases, caspase-3, 6, and 7 are key effector caspases that cleave multiple protein substrates in cells, leading irreversibly to cell death. Cellular caspase activity can be measured using caspase substrates.

WO2010022076 disclosed the following triazolopyridine derivatives for use as PIM kinase inhibitors, wherein $A=OR_{10}$ or $NR_{11}R_{12}$; B=H, F, Cl, OH, etc; $R_6$=H, F, Br, Me, CN, Ph, etc.

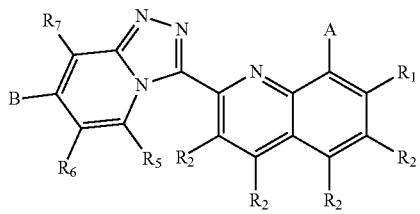

SUMMARY OF THE INVENTION

The invention provides novel 3-aryl-6-aryl-[1,2,4]triazolo[4,3-a]pyridines, as represented in Formulae I and II. These compounds have antiproliferative activities.

The present invention also provides pharmaceutical compositions comprising a compound of Formula I or II in an effective amount to treat or ameliorate diseases caused by uncontrolled cell proliferation in a mammal.

The invention also relates to the use of the compounds of Formula I or II for treating, preventing or ameliorating diseases caused by uncontrolled cell proliferation in a mammal, in particular, neoplasia and cancer.

The invention also provides a pharmaceutical composition useful for treating disorders responsive to these antiproliferative agents, containing an effective amount of a compound of one of the Formula I or II in admixture with one or more pharmaceutically acceptable carriers or diluents.

The invention also is directed to methods for the preparation of novel compounds of Formulae I and II.

DETAILED DESCRIPTION OF THE INVENTION

The inhibitors of cell proliferation of the present invention include 3-aryl-6-aryl-[1,2,4]triazolo[4,3-a]pyridines, as represented in Formulae I and II. Therefore, compounds of Formulae I and II are useful for treating disorders responsive to antiproliferative agents.

Specifically, compounds of the present invention are represented by Formula I:

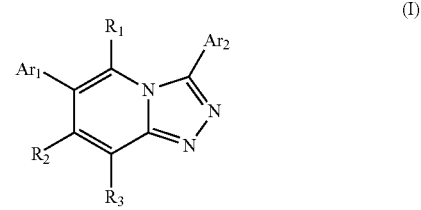

or pharmaceutically acceptable salts or prodrugs thereof, wherein:

$Ar_1$ and $Ar_2$ independently are an optionally substituted aryl or an optionally substituted heteroaryl;

$R_1$-$R_3$ independently are hydrogen, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, carbonylamido or optionally substituted alkylthiol;

with the proviso that $Ar_2$ is not 8-substituted-quinolin-2-yl when $Ar_1$ is phenyl.

Preferred compounds of Formula I include compounds wherein $Ar_1$ and $Ar_2$ are phenyl, naphthyl, pyridyl, quinolyl, isoquinolyl, isoxazolyl, pyrazolyl, imidazolyl, thienyl, furyl or pyrrolyl, each of which is optionally substituted. More preferably, $Ar_1$ and $Ar_2$ are phenyl or pyridyl. Another group of preferred compounds of Formula I include compounds wherein $R_1$, $R_2$ and $R_3$ are hydrogen.

One group of preferred compounds of the present invention are represented by Formula II:

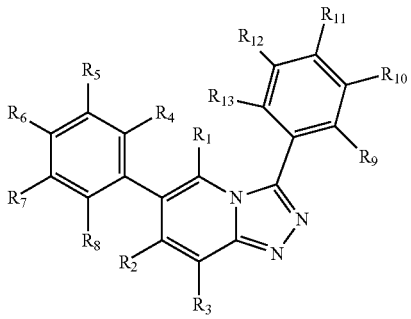

(II)

or pharmaceutically acceptable salts or prodrugs thereof, wherein:

$R_1$-$R_3$ independently are hydrogen, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, carbonylamido or optionally substituted alkylthiol;

$R_4$-$R_{13}$ independently are hydrogen, halo, amino, alkoxy, $C_{1-10}$ alkyl, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, nitro, cyano, acylamido, hydroxy, thiol, acyloxy, azido, carboxy, carbonylamido, alkylsulfonyl, aminosulfonyl, dialkylaminosulfonyl, alkylsulfiniyl, or alkylthiol; or $R_4$ and $R_5$, or $R_5$ and $R_6$, or $R_6$ and $R_7$, or $R_7$ and $R_8$, or $R_9$ and $R_{10}$, or $R_{10}$ and $R_{11}$, or $R_{11}$ and $R_{12}$, or $R_{12}$ and $R_{13}$, taken together with the atoms to which they are attached to form an aryl, heteroaryl, partially saturated carbocyclic or partially saturated heterocyclic group, wherein said group is optionally substituted.

One group of preferred compounds of Formula II include compounds wherein $R_4$ and $R_5$, or $R_5$ and $R_6$, or $R_6$ and $R_7$, or $R_7$ and $R_8$, or $R_9$ and $R_{10}$, or $R_{10}$ and $R_{11}$, or $R_{11}$ and $R_{12}$, or $R_{12}$ and $R_{13}$ are taken together to form a structure selected from the group consisting of —OCH$_2$O—, —(CH$_2$)$_3$—, —(CH$_2$)$_4$—, —OCH$_2$CH$_2$O—, —CH$_2$N(R$_{14}$)CH$_2$—, —CH$_2$CH$_2$N(R$_{14}$)CH$_2$—, —CH$_2$N(R$_{14}$)—CH$_2$CH$_2$—, —N(R$_{14}$)—CH═CH—, —CH═CH—N(R$_{14}$)—, —N(R$_{14}$)—CH$_2$—CH$_2$—, —CH$_2$—CH$_2$—N(R$_{14}$)—, —N(R$_{14}$)—CH═N—, —N═CH—N(R$_{14}$)—, —O—CH═CH—, —CH═CH—O—, —S—CH═CH—, —CH═CH—S—, —N—C(═O)—O—, —N—CH$_2$—CH$_2$—N— and —N═CH—CH═N—, wherein $R_{14}$ is hydrogen, $C_{1-10}$-alkyl, haloalkyl, alkenyl, alkynyl, hydroxyalkyl or aminoalkyl.

Exemplary preferred compounds of Formulae I and II include, without limitation:

3-(2-Methoxyphenyl)-6-(4-methoxyphenyl)-[1,2,4]triazolo[4,3-a]pyridine;
3-(2-Methoxyphenyl)-6-(3-methoxyphenyl)-[1,2,4]triazolo[4,3-a]pyridine;
3,6-Bis(2-methoxyphenyl)-[1,2,4]triazolo[4,3-a]pyridine;
6-(2-Fluoro-4-methylphenyl)-3-(2-methoxyphenyl)-[1,2,4]triazolo[4,3-a]pyridine;
6-(4-Methoxy-3-methylphenyl)-3-(2-methoxyphenyl)-[1,2,4]triazolo[4,3-a]pyridine;
6-(4-Isopropoxyphenyl)-3-(2-methoxyphenyl)-[1,2,4]triazolo[4,3-a]pyridine;
6-(4-Ethylphenyl)-3-(2-methoxyphenyl)-[1,2,4]triazolo[4,3-a]pyridine;
6-(4-Methoxy-2-methylphenyl)-3-(2-methoxyphenyl)-[1,2,4]triazolo[4,3-a]pyridine;
6-(4-Benzyloxy-3-methoxyphenyl)-3-(2-methoxyphenyl)-[1,2,4]triazolo[4,3-a]pyridine;
3-(2-Methoxyphenyl)-6-(4-methyl-3-nitrophenyl)-[1,2,4]triazolo[4,3-a]pyridine;
3-(2-Methoxyphenyl)-6-(4-trifluoromethoxyphenyl)-[1,2,4]triazolo[4,3-a]pyridine;
6-(3-Hydroxyphenyl)-3-(2-methoxyphenyl)-[1,2,4]triazolo[4,3-a]pyridine;
6-(4-Hydroxyphenyl)-3-(2-methoxyphenyl)-[1,2,4]triazolo[4,3-a]pyridine;
6-(Benzo[d][1,3]dioxol-5-yl)-3-(2-methoxyphenyl)-[1,2,4]triazolo[4,3-a]pyridine;
3-(2-Methoxyphenyl)-6-(6-methoxypyridin-3-yl)-[1,2,4]triazolo[4,3-a]pyridine;
6-(4-Ethoxy-3-methylphenyl)-3-(2-methoxyphenyl)-[1,2,4]triazolo[4,3-a]pyridine;
6-(4-Dimethylaminophenyl)-3-(2-methoxyphenyl)-[1,2,4]triazolo[4,3-a]pyridine;
3-(2-Methoxyphenyl)-6-(2-methoxypyrimidin-5-yl)-[1,2,4]triazolo[4,3-a]pyridine;
6-(3-Chloro-4-methylphenyl)-3-(2-methoxyphenyl)-[1,2,4]triazolo[4,3-a]pyridine;
6-(3-Hydroxy-4-methoxyphenyl)-3-(2-methoxyphenyl)-[1,2,4]triazolo[4,3-a]pyridine;
6-(3-Methoxy-4-nitrophenyl)-3-(2-methoxyphenyl)-[1,2,4]triazolo[4,3-a]pyridine;
3-(2-Methoxyphenyl)-6-(4-methylphenyl)-[1,2,4]triazolo[4,3-a]pyridine;
3-(2-Methoxyphenyl)-6-(3-methylphenyl)-[1,2,4]triazolo[4,3-a]pyridine;
3-(2-Methoxyphenyl)-6-phenyl-[1,2,4]triazolo[4,3-a]pyridine;
6-(2,4-Dimethylphenyl)-3-(2-methoxyphenyl)-[1,2,4]triazolo[4,3-a]pyridine;
6-(3-Chloro-4-methoxyphenyl)-3-(2-methoxyphenyl)-[1,2,4]triazolo[4,3-a]pyridine;
3-(2-Methoxyphenyl)-6-(4-trifluoromethylphenyl)-[1,2,4]triazolo[4,3-a]pyridine;
6-(3-Methoxy-4-methylphenyl)-3-(2-methoxyphenyl)-[1,2,4]triazolo[4,3-a]pyridine;
3-(2-Methoxyphenyl)-6-(3,4,5-trimethoxyphenyl)-[1,2,4]triazolo[4,3-a]pyridine;
6-(3,5-Dimethyl-4-methoxyphenyl)-3-(2-methoxyphenyl)-[1,2,4]triazolo[4,3-a]pyridine;
6-(3,4-Dimethoxyphenyl)-3-(2-methoxyphenyl)-[1,2,4]triazolo[4,3-a]pyridine;
6-(3,4-Dimethylphenyl)-3-(2-methoxyphenyl)-[1,2,4]triazolo[4,3-a]pyridine;
6-(3-Fluoro-4-methylphenyl)-3-(2-methoxyphenyl)-[1,2,4]triazolo[4,3-a]pyridine;
6-(4-Hexyloxyphenyl)-3-(2-methoxyphenyl)-[1,2,4]triazolo[4,3-a]pyridine;
6-(3-Fluoro-4-methoxyphenyl)-3-(2-methoxyphenyl)-[1,2,4]triazolo[4,3-a]pyridine;
6-(2,4-Dimethoxyphenyl)-3-(2-methoxyphenyl)-[1,2,4]triazolo[4,3-a]pyridine;
6-(4-Benzyloxy-3-methylphenyl)-3-(2-methoxyphenyl)-[1,2,4]triazolo[4,3-a]pyridine;
6-(4-Ethoxyphenyl)-3-(2-methoxyphenyl)-[1,2,4]triazolo[4,3-a]pyridine;
3-(2-Methoxyphenyl)-6-(4-nitrophenyl)-[1,2,4]triazolo[4,3-a]pyridine;

6-(4-Methoxy-3-nitrophenyl)-3-(2-methoxyphenyl)-[1,2,4]triazolo[4,3-a]pyridine;
6-(4-Hydroxy-3-methylphenyl)-3-(2-methoxyphenyl)-[1,2,4]triazolo[4,3-a]pyridine;
6-(4-Methoxy-3-nitrophenyl)-3-(2-methoxy-5-nitrophenyl)-[1,2,4]triazolo[4,3-a]pyridine;
6-(4-Amino-3-methoxyphenyl)-3-(2-methoxyphenyl)-[1,2,4]triazolo[4,3-a]pyridine;
6-(3-Amino-4-methylphenyl)-3-(2-methoxyphenyl)-[1,2,4]triazolo[4,3-a]pyridine;
6-(3-Aminophenyl)-3-(2-methoxyphenyl)-[1,2,4]triazolo[4,3-a]pyridine hydrochloride;
6-(3-Amino-4-methoxyphenyl)-3-(2-methoxyphenyl)-[1,2,4]triazolo[4,3-a]pyridine hydrochloride;
6-(4-Aminophenyl)-3-(2-methoxyphenyl)-[1,2,4]triazolo[4,3-a]pyridine hydrochloride;
6-(4-Methylaminophenyl)-3-(2-methoxyphenyl)-[1,2,4]triazolo[4,3-a]pyridine hydrochloride;
3-(4-Chloro-2-methoxyphenyl)-6-(3-fluoro-4-methoxyphenyl)-[1,2,4]triazolo[4,3-a]pyridine;
6-(3-Amino-4-methoxyphenyl)-3-(4-chloro-2-methoxyphenyl)-[1,2,4]triazolo[4,3-a]pyridine;
6-(3-Hydroxy-4-methoxyphenyl)-3-(2-methoxy-4-methylphenyl)-[1,2,4]triazolo[4,3-a]pyridine;
6-(3-Amino-4-methoxyphenyl)-3-(2-methoxy-4-methylphenyl)-[1,2,4]triazolo[4,3-a]pyridine;
6-(3-Fluoro-4-methoxyphenyl)-3-(2-methoxy-4-methylphenyl)-[1,2,4]triazolo[4,3-a]pyridine;
3-(2-Methoxyphenyl)-6-(4-methoxyphenyl)-7-methyl-[1,2,4]triazolo[4,3-a]pyridine;
3-(2-Methoxyphenyl)-6-(4-methoxyphenyl)-8-methyl-[1,2,4]triazolo[4,3-a]pyridine;
6-(4-Hydroxy-3-methoxyphenyl)-3-(2-methoxyphenyl)-[1,2,4]triazolo[4,3-a]pyridine;
3-(4-Chloro-2-methoxyphenyl)-6-(4-methoxyphenyl)-[1,2,4]triazolo[4,3-a]pyridine;
3-(4-Fluoro-2-methoxyphenyl)-6-(4-methoxyphenyl)-[1,2,4]triazolo[4,3-a]pyridine;
3-(4-Bromo-2-methoxyphenyl)-6-(4-methoxyphenyl)-[1,2,4]triazolo[4,3-a]pyridine;
3-(2-Methoxy-4-trifluoromethylphenyl)-6-(4-methoxyphenyl)-[1,2,4]triazolo[4,3-a]pyridine;
3-(2,6-Dimethoxyphenyl)-6-(4-methoxyphenyl)-[1,2,4]triazolo[4,3-a]pyridine;
3-(2,5-Dimethoxyphenyl)-6-(4-methoxyphenyl)-[1,2,4]triazolo[4,3-a]pyridine;
3-(6-Fluoro-2-methoxyphenyl)-6-(4-methoxyphenyl)-[1,2,4]triazolo[4,3-a]pyridine;
3,6-Bis(4-methoxyphenyl)-[1,2,4]triazolo[4,3-a]pyridine;
3-(3-Bromo-2,6-dimethoxyphenyl)-6-(4-methoxyphenyl)-[1,2,4]triazolo[4,3-a]pyridine;
3-(2-Methoxy-4-methylphenyl)-6-(4-methoxyphenyl)-[1,2,4]triazolo[4,3-a]pyridine;
6-(4-Methoxyphenyl)-3-(2-trifluoromethoxyphenyl)-[1,2,4]triazolo[4,3-a]pyridine;
6-(4-Methoxyphenyl)-3-phenyl-[1,2,4]triazolo[4,3-a]pyridine;
6-(4-Methoxyphenyl)-3-(2,4,5-trimethoxyphenyl)-[1,2,4]triazolo[4,3-a]pyridine;
3-(2-Methoxy-4-nitrophenyl)-6-(4-methoxyphenyl)-[1,2,4]triazolo[4,3-a]pyridine;
3-(2,4-Dimethoxyphenyl)-6-(4-methoxyphenyl)-[1,2,4]triazolo[4,3-a]pyridine;
6-(4-Methoxyphenyl)-3-(2,3,4-trimethoxyphenyl)-[1,2,4]triazolo[4,3-a]pyridine;
3-(2,3-Dimethoxyphenyl)-6-(4-methoxyphenyl)-[1,2,4]triazolo[4,3-a]pyridine;
3-(2-Ethoxyphenyl)-6-(4-methoxyphenyl)-[1,2,4]triazolo[4,3-a]pyridine;
6-(4-Methoxyphenyl)-3-(2-methoxy-5-sulfamoylphenyl)-[1,2,4]triazolo[4,3-a]pyridine;
3-(2-Methoxy-5-methylphenyl)-6-(4-methoxyphenyl)-[1,2,4]triazolo[4,3-a]pyridine;
3-(3-Methoxyphenyl)-6-(4-methoxyphenyl)-[1,2,4]triazolo[4,3-a]pyridine;
6-(4-Methoxyphenyl)-3-(2-methylphenyl)-[1,2,4]triazolo[4,3-a]pyridine;
6-(4-Methoxyphenyl)-3-(2-methylaminophenyl)-[1,2,4]triazolo[4,3-a]pyridine;
3-(2-Dimethylaminophenyl)-6-(4-methoxyphenyl)-[1,2,4]triazolo[4,3-a]pyridine;
6-(3-Amino-4-methoxyphenyl)-3-(4-chloro-2-methoxyphenyl)-[1,2,4]triazolo[4,3-a]pyridine hydrochloride;
6-(3-Amino-4-methoxyphenyl)-3-(2-methoxy-4-methylphenyl)-[1,2,4]triazolo[4,3-a]pyridine hydrochloride;
3-(4-Chloro-2-methoxyphenyl)-6-(4-methoxyphenyl)-[1,2,4]triazolo[4,3-a]pyridine hydrochloride;
3-(2-Methoxy-4-methylphenyl)-6-(4-methoxyphenyl)-[1,2,4]triazolo[4,3-a]pyridine hydrochloride;
3-(2-Chloropyridin-3-yl)-6-(4-methoxyphenyl)-[1,2,4]triazolo[4,3-a]pyridine;
6-(4-Methoxyphenyl)-3-(2-methoxypyridin-3-yl)-[1,2,4]triazolo[4,3-a]pyridine;
3-(4-Amino-2-methoxyphenyl)-6-(4-methoxyphenyl)-[1,2,4]triazolo[4,3-a]pyridine hydrochloride;
3-(4-Chloro-2-methoxyphenyl)-6-(4-methylaminophenyl)-[1,2,4]triazolo[4,3-a]pyridine;
3-(4-Chloro-2-methoxyphenyl)-6-(3-hydroxy-4-methoxyphenyl)-[1,2,4]triazolo[4,3-a]pyridine;
6-(3-Amino-4-methylphenyl)-3-(4-chloro-2-methoxyphenyl)-[1,2,4]triazolo[4,3-a]pyridine;
6-(3-Amino-4-methylphenyl)-3-(4-methyl-2-methoxyphenyl)-[1,2,4]triazolo[4,3-a]pyridine;
6-(4-Methylaminophenyl)-3-(4-methyl-2-methoxyphenyl)-[1,2,4]triazolo[4,3-a]pyridine;

and pharmaceutically acceptable salts or prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "amino" as employed herein by itself or as part of another group is primary (—NH$_2$), secondary (—NHR), or tertiary (—NRR), wherein R is independently an optionally substituted alkyl, aryl, heteroaryl, or two R groups together with the nitrogen form a 5 or 6 membered heterocyclic group, optionally containing an additional N or O atom.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$alkyl groups mentioned above, which may be optionally substituted. Alkoxy substituents include, without limitation, halo, morpholino, amino including alkylamino and dialkylamino, and carboxy including esters thereof.

Useful alkylthio groups include sulfur substituted by one of the $C_{1-10}$ alkyl groups mentioned above, which may be optionally substituted. Also included are the sulfoxides and sulfones of such alkylthio groups.

Useful amino and optionally substituted amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

Optional substituents on the alkyl, alkoxy, alkylthio, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, methylenedioxy, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$) alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carboxy, di($C_{1-10}$-alkyl) amino, alkylsulfonyl, aminosulfonyl, dialkylaminosulfonyl, or alkylsulfiniyl.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_{3-8}$cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, or 14 it electrons shared in a cyclic array; and containing, as ring atom, carbon atoms and 1-3 heteroatoms selected from oxygen, nitrogen and sulfur.

Useful heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, (3-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, tetrahydrocyclopenta[c]pyrazol-3-yl, pyrazolo[1, 5-a]pyrimidinyl, 1,2-benzoisoxazol-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$-carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formula I or II can be prepared as illustrated by the exemplary reaction in Scheme 1. Reaction of a 2,5-dihalopyridine, such as 5-bromo-2-chloropyridine, and hydrazine produced 5-bromo-2-hydrazinylpyridine. Reaction of 5-bromo-2-hydrazinylpyridine with a substituted benzoic acid, such as 2-methoxybenzoic acid, in the presence of coupling agents, such as BOP and NMM, produced N-(5-bromopyridin-2-yl)-2-methoxybenzohydrazide. Treatment of N-(5-bromopyridin-2-yl)-2-methoxybenzohydrazide with phosphorus oxychloride produced the cyclized product 6-bromo-3-(2-methoxyphenyl)-[1,2,4]triazolo[4,3-a]pyridine. Coupling of 6-bromo-3-(2-methoxyphenyl)-[1,2,4]triazolo[4,3-a]pyridine with a substituted phenylboronic acid, such as 4-methoxyphenylboronic acid, in the presence of a palladium catalyst, such as tetrakis(triphenylphosphine)palladium, produced 3-(2-methoxyphenyl)-6-(4-methoxyphenyl)-[1,2,4]triazolo[4,3-a]pyridine.

Scheme 1

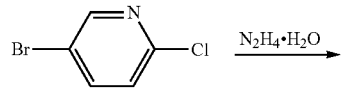

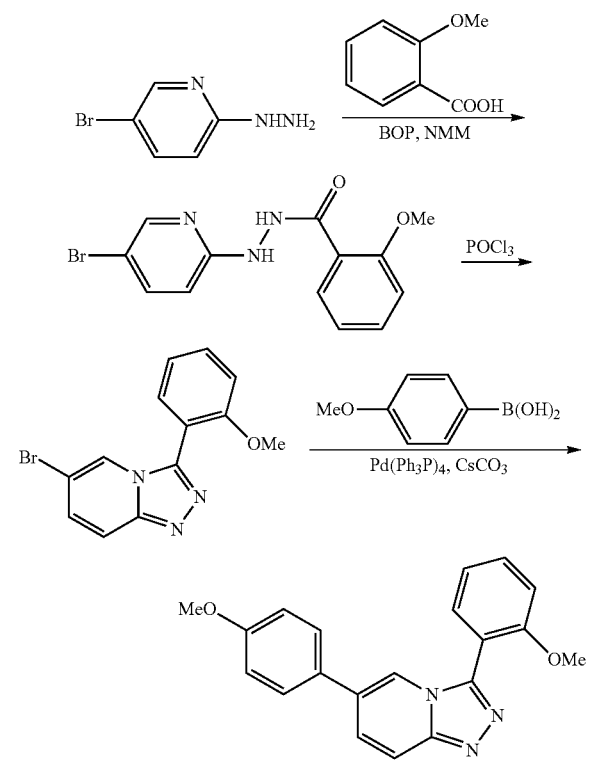

Compounds of this invention can be prepared as illustrated by the exemplary reaction in Scheme 2. Coupling of a 2,5-dihalopyridine, such as 5-bromo-2-chloropyridine, with a substituted phenylboronic acid, such as 4-methoxyphenylboronic acid, in the presence of a palladium catalyst, such as tetrakis(triphenylphosphine)palladium, produced 2-chloro-5-(4-methoxyphenyl)pyridine. Reaction of 2-chloro-5-(4-methoxyphenyl)pyridine with hydrazine produced 2-hydrazinyl-5-(4-methoxyphenyl)pyridine. Reaction of 2-hydrazinyl-5-(4-methoxyphenyl)pyridine with a substituted benzoic acid, such as 4-chloro-2-methoxybenzoic acid, in the presence of coupling agents, such as BOP (benzotriazole-1-yl-oxy-tris-(dimethylamino)-phosphonium hexafluorophosphate) and NMM (N-methylmorpholine), produced 4-chloro-2-methoxy-N-(5-(4-methoxyphenyl)pyridin-2-yl)-benzohydrazide. Treatment of 4-chloro-2-methoxy-N-(5-(4-methoxyphenyl)pyridin-2-yl)-benzohydrazide with phosphorus oxychloride produced the cyclized product 3-(4-chloro-2-methoxyphenyl)-6-(4-methoxyphenyl)-[1,2,4]triazolo[4,3-a]pyridine, which can be converted into a salt by treatment with HCl in ethyl acetate.

Scheme 2

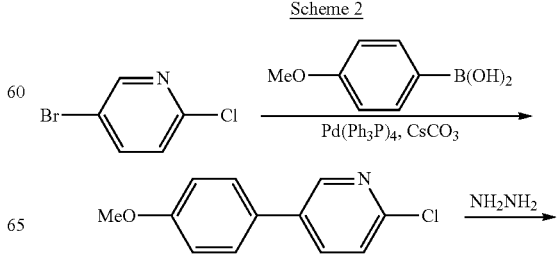

-continued

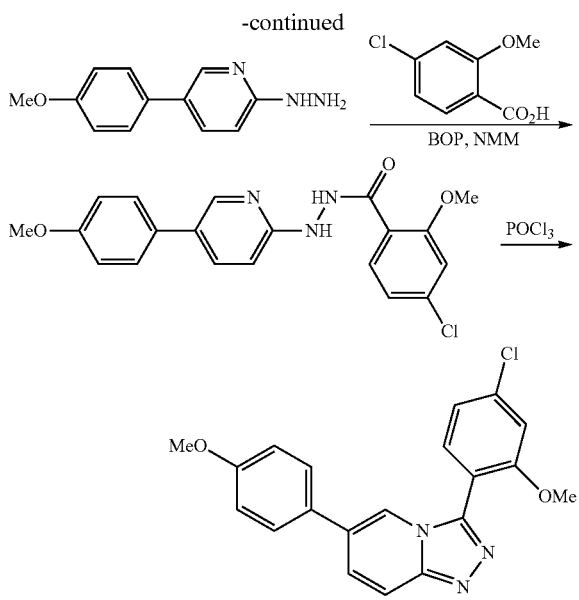

An important aspect of the present invention is the discovery that compounds having Formula I or II are antiproliferative agents. Therefore, these compounds are useful in a variety of clinical conditions in which there is uncontrolled cell proliferation and spread of abnormal cells, such as in the case of cancer.

Another important aspect of the present invention is the discovery that compounds having Formula I or II are potent and highly efficacious antiproliferative agents in drug resistant cancer cells, such as breast and prostate cancer cells, which enables these compounds to kill these drug resistant cancer cells. In comparison, many standard anticancer drugs are not effective in killing drug resistant cancer cells under the same conditions. Therefore, compounds of this invention are useful for the treatment of drug resistant cancer, such as breast cancer in mammals.

The present invention includes a therapeutic method comprising administering to a mammal an effective amount of a compound, or a pharmaceutically acceptable salt or prodrug of said compound of Formula I or II, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds of Formula I or II formulated for oral, intravenous, local and topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

In another embodiment, a pharmaceutical composition comprising a compound of Formula I or II or a pharmaceutically acceptable salt thereof, which functions as an antiproliferative agent, in combination with a pharmaceutically acceptable vehicle, is provided.

Another embodiment of the present invention is directed to a composition effective to inhibit neoplasia comprising a compound, or a pharmaceutically acceptable salt or prodrug of said compound of Formula I or II, which functions as an antiproliferative agent, in combination with at least one known anticancer agent, or a pharmaceutically acceptable salt of said agent. Examples of known anticancer agents which may be used for combination therapy include, but not are limited to alkylating agents, such as busulfan, cis-platin, mitomycin C, and carboplatin; antimitotic agents, such as colchicine, vinblastine, paclitaxel, and docetaxel; topoisomerase I inhibitors, such as camptothecin and topotecan; topoisomerase II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; antibodies, such as campath, Herceptin®, Rituxan®. Other known anticancer agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, arsenic trioxide, gemcitabine, letrozole, fulvestrant, bendamustine, pralatrexate, pemetrexed, nelarabine, temozolomide, zoledronic acid, irinotecan, ixabepilone, cabazitaxel, vinorelbine, Panitumumab, Ofatumumab Avastin, imatinib, gefitinib, erlotinib, lapatinib, sorafenib, sunitinib, nilotinib, dasatinib, pazopanib, bortezomib, vorinostat, romidepsin, temsirolimus, everolimus, thalidomide, lenalidomide and alanosine.

In practicing the methods of the present invention, the compound of the invention may be administered together with at least one known anticancer agent as part of a unitary pharmaceutical composition. Alternatively, the compound of the invention may be administered apart from at least one known anticancer agent. In one embodiment, the compound of the invention and at least one known anticancer agent are administered substantially simultaneously, i.e. the compounds are administered at the same time or one after the other, so long as the compounds reach therapeutic levels in the blood at the same time. In another embodiment, the compound of the invention and at least one known anticancer agent are administered according to their individual dose schedule, so long as the compounds reach therapeutic levels in the blood.

Another embodiment of the present invention is directed to a composition effective to inhibit neoplasia comprising a bioconjugate of a compound described herein, which functions as an antiproliferative agent, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective to inhibit neoplasia comprising a compound of Formula I or II, or its pharmaceutically acceptable salt or prodrug, which functions as an antiproliferative agent, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound of Formula I or II, or its pharmaceutically acceptable salt or prodrug, which functions as an antiproliferative agent. The invention also relates to a method of treating cancer by surgically removing the cancer and then treating the mammal with one of the pharmaceutical compositions described herein.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull.* 59:227-248 (2001)). Therefore, antiproliferative agents of the present invention are useful as therapeutics for the prevention or reduction of in-stent restenosis.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. If a known anticancer agent is also administered, it is administered in an amount that is effective to achieve its intended purpose. The amounts of such known anticancer agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any mammal, which may experience the beneficial effects of the compounds of the invention. Foremost among such mammals are humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray interface. $^1$H spectra was recorded at 300 MHz and at 300° K, on a Brucker AMX 300 apparatus. Chemical shifts were recorded as parts per million (ppm) downfield from TMS (0.00 ppm), and J coupling constants were reported in hertz (Hz).

Example 1

3-(2-Methoxyphenyl)-6-(4-methoxyphenyl)-[1,2,4]triazolo[4,3-a]pyridine a) 5-Bromo-2-hydrazinylpyridine A mixture of 5-bromo-2-chloropyridine (11.5 g, 60 mmol) and hydrazine hydrate (100 mL) was refluxed under Argon for 2 h. The mixture was cooled to room temperature, filtered and the solids were washed with water (50 mL×3), dried to give the title compound (8.30 g, 74.4% yield) as yellow solids. MS: m/z 188.0 [M+H$^+$].

b) N-(5-Bromopyridin-2-yl)-2-methoxybenzohydrazide

To a solution of 5-bromo-2-hydrazinylpyridine (7.1 g, 38 mmol) and 2-methoxybenzoic acid (7.0 g, 46 mmol) in dichloromethane (DCM, 100 mL) were added benzotriazole-1-yl-oxy-tris-(dimethylamino)-phosphonium hexafluorophosphate (BOP, 25.2 g, 57 mmol) and N-methylmorpholine (NMM, 13.4 g, 0.10 mol), and it was stirred at room temperature for 2 h. The mixture was filtered and the solids were washed with DCM (50 mL×3), dried to give the title compound (8.23 g, 67.5% yield) as yellow solids. MS: m/z 322.1 [M+H$^+$].

c) 6-Bromo-3-(2-methoxyphenyl)-[1,2,4]triazolo[4,3-a]pyridine

A flask was charged with N-(5-bromopyridin-2-yl)-2-methoxybenzohydrazide (5.0 g, 15.6 mmol) and phosphorus oxychloride (POCl$_3$, 50 mL). The mixture was stirred at 100° C. for 10 h, and then was added to about 200 g of ice. The mixture was adjusted to pH 9 with solid sodium bicarbonate (NaHCO$_3$). The precipitate was collected by filtration to give the crude product. The crude product was purified by column chromatography on silica gel (petroleum ether:ethyl acetate=1:1) to give the title compound (2.8 g, 59% yield) as yellow solids. $^1$H NMR (DMSO-d$_6$): 8.28 (m, 1H), 7.86 (dd, J=9.6 and 0.9 Hz, 1H), 7.65-7.52 (m, 3H), 7.30 (d, J=8.1 Hz, 1H), 7.19 (m, 1H), 3.84 (s, 3H).

d) 3-(2-Methoxyphenyl)-6-(4-methoxyphenyl)-[1,2,4]triazolo[4,3-a]pyridine

A flask was charged with 6-bromo-3-(2-methoxyphenyl)-[1,2,4]triazolo[4,3-a]pyridine (151 mg, 0.5 mmol), 4-methoxyphenylboronic acid (80 mg, 0.5 mmol), tetrakis(triphenylphosphine)palladium (Pd(PPh$_3$)$_4$, 5.8 mg, 0.005 mmol), cesium carbonate (Cs$_2$CO$_3$, 326 mg, 1.0 mmol), 1,4-dioxane (10 mL) and water (2 mL). The mixture was stirred at 100° C. under Argon for 10 h. The mixture was evaporated to afford the crude product. The crude product was purified by column chromatography on silica gel (petroleum ether:ethyl acetate=1:1) to give the title compound (140 mg, 84.2% yield) as yellow solids. $^1$H NMR (DMSO-d$_6$): 8.06 (m, 1H), 7.90 (dd, J=9.5 and 0.9 Hz, 1H), 7.75 (dd, J=9.6 and 1.8 Hz, 1H), 7.67-7.62 (m, 4H), 7.32 (d, J=8.1 Hz, 1H), 7.19 (t, J=7.5 Hz, 1H), 7.03 (d, J=8.7 Hz, 2H), 3.85 (s, 3H), 3.80 (s, 3H). MS: m/z 332.2 [M+H$^+$].

The following compounds were prepared from 6-bromo-3-(2-methoxyphenyl)-[1,2,4]triazolo[4,3-a]pyridine and the corresponding phenylboronic acid, or pyridylboronic acid, or pyrimidylboronic acid using a procedure similar to those described for the synthesis of Example 1d.

Example 2

3-(2-Methoxyphenyl)-6-(3-methoxyphenyl)-[1,2,4]triazolo[4,3-a]pyridine $^1$H NMR (DMSO-d$_6$): 8.16 (m, 1H), 7.94 (dd, J=9.6 and 1.2 Hz, 1H), 7.79 (dd, J=9.6 and 1.5 Hz, 1H), 7.67-7.61 (m, 2H), 7.43-7.17 (m, 5H), 6.99 (m, 1H), 3.87 (s, 3H), 3.83 (s, 3H). MS: m/z 332.2 [M+H$^+$].

Example 3

3,6-Bis(2-methoxyphenyl)-[1,2,4]triazolo[4,3-a]pyridine $^1$H NMR (DMSO-d$_6$): 7.93 (m, 1H), 7.86 (dd, J=9.6 and 1.2 Hz, 1H), 7.65-7.56 (m, 3H), 7.44-7.35 (m, 2H), 7.29 (d, J=8.1 Hz, 1H), 7.20-7.14 (m, 2H), 7.05 (m, 1H), 3.84 (s, 3H), 3.79 (s, 3H). MS: m/z 332.2 [M+H$^+$].

Example 4

6-(2-Fluoro-4-methylphenyl)-3-(2-methoxyphenyl)-[1,2,4]triazolo[4,3-a]pyridine $^1$H NMR (DMSO-d$_6$): 8.07 (s, 1H), 7.94 (d, J=9.6 and 1.2 Hz, 1H), 7.63-7.61 (m, 3H), 7.50 (t, J=8.1 Hz, 1H), 7.30 (d, J=8.1 Hz, 1H), 7.21-7.13 (m, 3H), 3.83 (s, 3H), 2.36 (s, 3H). MS: m/z 334.2 [M+H$^+$].

Example 5

6-(4-Methoxy-3-methylphenyl)-3-(2-methoxyphenyl)-[1,2,4]triazolo[4,3-a]pyridine $^1$H NMR (DMSO-d$_6$): 8.04 (m, 1H), 7.91 (dd, J=9.6 and 0.9 Hz, 1H), 7.75 (dd, J=9.6 and 1.5 Hz, 1H), 7.68-7.62 (m, 2H), 7.53-7.49 (m, 2H), 7.32 (d, J=8.1 Hz, 1H), 7.20 (t, J=8.0 Hz, 1H), 7.03 (d, J=9.0 Hz, 1H), 3.86 (s, 3H), 3.82 (s, 3H), 2.21 (s, 3H). MS: m/z 346.2 [M+H$^+$].

Example 6

6-(4-Isopropoxyphenyl)-3-(2-methoxyphenyl)-[1,2,4]triazolo[4,3-a]pyridine $^1$H NMR (DMSO-d$_6$): 8.05 (m, 1H), 7.91 (dd, J=9.6 and 0.9 Hz, 1H), 7.75 (dd, J=9.6 and 1.5 Hz, 1H), 7.64-7.59 (m, 4H), 7.32 (d, J=8.4 Hz, 1H), 7.19 (t, J=7.5 Hz, 1H), 7.01 (d, J=9.0 Hz, 2H), 4.66 (m, 1H), 3.85 (s, 3H), 1.28 (d, J=6.0 Hz, 6H). MS: m/z 360.2 [M+H$^+$].

Example 7

6-(4-Ethylphenyl)-3-(2-methoxyphenyl)-[1,2,4]triazolo[4,3-a]pyridine $^1$H NMR (DMSO-d$_6$): 8.10 (m, 1H), 7.94 (dd, J=9.5 and 1.2 Hz, 1H), 7.77 (dd, J=10.5 and 1.8 Hz, 1H), 7.64-7.60 (m, 4H), 7.34-7.30 (m, 3H), 7.19 (t, J=7.5 Hz, 1H), 3.85 (s, 3H), 2.65 (q, J=7.5 Hz, 2H), 1.20 (t, J=7.5 Hz, 3H). MS: m/z 330.2 [M+H$^+$].

Example 8

6-(4-Methoxy-2-methylphenyl)-3-(2-methoxyphenyl)-[1,2,4]triazolo[4,3-a]pyridine $^1$H NMR (DMSO-d$_6$): 7.87 (dd, J=9.3 and 1.2 Hz, 1H), 7.77 (m, 1H), 7.64-7.59 (m, 2H), 7.42 (dd, J=9.5 and 1.5 Hz, 1H), 7.26 (d, J=8.1 Hz, 1H), 7.21-7.14 (m, 2H), 6.91 (m, 1H), 6.84 (m, 1H), 3.82 (s, 3H), 3.77 (s, 3H), 2.29 (s, 3H). MS: m/z 346.2 [M+H$^+$].

Example 9

6-(4-Benzyloxy-3-methoxyphenyl)-3-(2-methoxyphenyl)-[1,2,4]triazolo[4,3-a]pyridine $^1$H NMR (DMSO-d$_6$): 8.13 (m, 1H), 7.91 (dd, J=9.6 and 1.8 Hz, 1H), 7.78 (dd, J=9.6 and 1.8 Hz, 1H), 7.67-7.61 (m, 2H), 7.47-7.11 (m, 10H), 5.14 (s, 2H), 3.89 (s, 3H), 3.87 (s, 3H). MS: m/z 438.2 [M+H$^+$].

Example 10

3-(2-Methoxyphenyl)-6-(4-methyl-3-nitrophenyl)-[1,2,4]triazolo[4,3-a]pyridine $^1$H NMR (DMSO-d$_6$): 8.36 (m, 1H), 8.30 (d, J=1.8 Hz, 1H), 8.01-7.95 (m, 2H), 7.84 (dd, J=9.6 and 1.2 Hz, 1H), 7.68-7.59 (m, 3H), 7.22 (d, J=8.1 Hz, 1H), 7.20 (t, J=7.5 Hz, 1H), 3.85 (s, 3H), 2.54 (s, 3H). MS: m/z 361.2 [M+H$^+$].

Example 11

3-(2-Methoxyphenyl)-6-(4-trifluoromethoxyphenyl)-[1,2,4]trizolo[4,3-a]pyridine $^1$H NMR (DMSO-d$_6$): 8.22 (m, 1H), 7.96 (dd, J=9.6 and 1.2 Hz, 1H), 7.86-7.80 (m, 3H), 7.68-7.62 (m, 2H), 7.47 (d, J=8.1 Hz, 2H), 7.31 (d, J=8.1 Hz, 1H), 7.19 (t, J=8.0 Hz, 1H), 3.85 (s, 3H). MS: m/z 386.1 [M+H$^+$].

Example 12

6-(3-Hydroxyphenyl)-3-(2-methoxyphenyl)-[1,2,4]triazolo[4,3-a]pyridine $^1$H NMR (DMSO-d$_6$): 9.64 (s, 1H), 8.02 (m, 1H), 7.93 (dd, J=9.6 and 0.9 Hz, 1H), 7.74-7.61 (m, 3H), 7.32 (m, 1H), 7.27 (d, J=7.8 Hz, 1H), 7.20 (m, 1H), 7.10 (m, 1H), 7.02 (t, J=2.0 Hz, 1H), 6.83-6.80 (m, 1H), 3.86 (s, 3H). MS: m/z 318.1 [M+H$^+$].

Example 13

6-(4-Hydroxyphenyl)-3-(2-methoxyphenyl)-[1,2,4]triazolo[4,3-a]pyridine $^1$H NMR (DMSO-$d_6$): 9.66 (s, 1H), 7.99 (m, 1H), 7.89 (dd, J=9.6 and 0.9 Hz, 1H), 7.72 (dd, J=9.6 and 1.8 Hz, 1H), 7.64-7.60 (m, 2H), 7.51 (d, J=6.6 Hz, 2H), 7.33 (d, J=8.1 Hz, 1H), 7.19 (t, J=7.2 Hz, 1H), 6.86 (d, J=6.6 Hz, 2H), 3.85 (s, 3H). MS: m/z 318.2 [M+H$^+$].

Example 14

6-(Benzo[d][1,3]dioxol-5-yl)-3-(2-methoxyphenyl)-[1,2,4]triazolo[4,3-a]pyridine $^1$H NMR (DMSO-$d_6$): 8.08 (m, 1H), 7.90 (dd, J=9.6 and 0.9 Hz, 1H), 7.73 (dd, J=9.6 and 1.8 Hz, 1H), 7.67-7.60 (m, 2H), 7.32-7.29 (m, 2H), 7.21-7.17 (m, 2H), 7.01 (d, J=8.1 Hz, 1H), 6.07 (s, 2H), 3.84 (s, 3H). MS: m/z 346.2 [M+H$^+$].

Example 15

3-(2-Methoxyphenyl)-6-(6-methoxypyridin-3-yl)-[1,2,4]triazolo[4,3-a]pyridine $^1$H NMR (DMSO-$d_6$): 8.51 (d, J=2.1 Hz, 1H), 8.22 (s, 1H), 8.06 (dd, J=8.7 and 1.8 Hz, 1H), 7.95 (dd, J=9.6 and 0.9 Hz, 1H), 7.77 (dd, J=9.6 and 1.5 Hz, 1H), 7.67-7.62 (m, 2H), 7.31 (d, J=8.1 Hz, 1H), 7.19 (t, J=7.7 Hz, 1H), 6.93 (d, J=8.1 Hz, 1H), 3.90 (s, 3H), 3.86 (s, 3H). MS: m/z 333.2 [M+H$^+$].

Example 16

6-(4-Ethoxy-3-methylphenyl)-3-(2-methoxyphenyl)-[1,2,4]triazolo[4,3-a]pyridine $^1$H NMR (DMSO-$d_6$): 8.03 (s, 1H), 7.90 (d, J=8.7 Hz, 1H), 7.75 (m, 1H), 7.68-7.62 (m, 2H), 7.49-7.46 (m, 2H), 7.32 (d, J=8.1 Hz, 1H), 7.19 (t, J=8.0 Hz, 1H), 7.01 (d, J=9.0 Hz, 1H), 4.07 (q, J=6.9 Hz, 2H), 3.86 (s, 3H), 2.21 (s, 3H), 1.36 (t, J=6.9 Hz, 3H). MS: m/z 360.2 [M+H$^+$].

Example 17

6-(4-Dimethylaminophenyl)-3-(2-methoxyphenyl)-[1,2,4]triazolo[4,3-a]pyridine $^1$H NMR (DMSO-$d_6$): 7.96 (m, 1H), 7.88 (dd, J=9.6 and 0.9 Hz, 1H), 7.75 (dd, J=9.6 and 1.8 Hz, 1H), 7.68-7.60 (m, 2H), 7.55-7.50 (m, 2H), 7.32 (d, J=8.1 Hz, 1H), 7.19 (t, J=7.5 Hz, 1H), 6.83-6.77 (m, 2H), 3.86 (s, 3H), 2.94 (s, 6H). MS: m/z 345.2 [M+H$^+$].

Example 18

3-(2-Methoxyphenyl)-6-(2-methoxypyrimidin-5-yl)-[1,2,4]triazolo[4,3-a]pyridine $^1$H NMR (DMSO-$d_6$): 8.95 (s, 2H), 8.42 (m, 1H), 7.99 (dd, J=9.6 and 0.9 Hz, 1H), 7.80 (dd, J=9.6 and 1.5 Hz, 1H), 7.67-7.64 (m, 2H), 7.30 (d, J=8.1 Hz, 1H), 7.18 (t, J=7.1 Hz, 1H), 3.97 (s, 3H), 3.86 (s, 3H). MS: m/z 334.1 [M+H$^+$].

Example 19

6-(3-Chloro-4-methylphenyl)-3-(2-methoxyphenyl)-[1,2,4]triazolo[4,3-a]pyridine $^1$H NMR (DMSO-$d_6$): 8.23 (m, 1H), 7.93 (dd, J=9.6 and 1.5 Hz, 1H), 7.81-7.77 (m, 2H), 7.68-7.61 (m, 3H), 7.51 (m, 1H), 7.32 (d, J=7.8 Hz, 1H), 7.20 (m, 1H), 3.84 (s, 3H), 2.37 (s, 3H). MS: m/z 350.1 [M+H$^+$].

Example 20

6-(3-Hydroxy-4-methoxyphenyl)-3-(2-methoxyphenyl)-[1,2,4]triazolo[4,3-a]pyridine $^1$H NMR (DMSO-$d_6$): 9.23 (s, 1H), 7.94-7.88 (m, 2H), 7.72-7.61 (m, 3H), 7.33 (d, J=8.1 Hz, 1H), 7.20 (t, J=7.5 Hz, 1H), 7.11-7.00 (m, 3H), 3.86 (s, 3H), 3.80 (s, 3H). MS: m/z 348.2 [M+H$^+$].

Example 21

6-(3-Methoxy-4-nitrophenyl)-3-(2-methoxyphenyl)-[1,2,4]triazolo[4,3-a]pyridine $^1$H NMR (DMSO-$d_6$): 8.42 (m, 1H), 8.02-7.97 (m, 2H), 7.85 (m, 1H), 7.68-7.57 (m, 3H), 7.45 (m, 1H), 7.32 (m, 1H), 7.21 (m, 1H), 4.04 (s, 3H), 3.89 (s, 3H). MS: m/z 377.1 [M+H$^+$].

Example 22

3-(2-Methoxyphenyl)-6-(4-methylphenyl)-[1,2,4]triazolo[4,3-a]pyridine

To a solution of 6-bromo-3-(2-methoxyphenyl)-[1,2,4]triazolo[4,3-a]pyridine (100 mg, 0.329 mmol) in toluene (20 mL) and water (5 mL) was added 4-methylphenylboronic acid (67.1 mg, 0.493 mmol), Pd(PPh$_3$)$_4$ (18.4 mg, 0.016 mmol) and Cs$_2$CO$_3$ (55.3 mg, 0.658 mmol), and the reaction mixture was refluxed under Argon overnight. The mixture was filtered and the filtrate was washed with water (50 mL×2), dried over anhydrous Na$_2$SO$_4$ and concentrated to dryness. The residue was purified by column chromatography on silica gel (petroleum ether:ethyl acetate=1:1) to give the title compound (89.5 mg, 50.6% yield) as yellow solids. $^1$H NMR (DMSO-$d_6$): 8.09 (m, 1H), 7.93 (dd, J=9.6 and 0.9 Hz, 1H), 7.77 (d, J=9.6 and 1.8 Hz, 1H), 7.64-7.58 (m, 4H), 7.33-7.28 (m, 3H), 7.19 (t, J=7.2 Hz, 1H), 3.85 (s, 3H), 2.35 (s, 3H). MS: m/z 316.2 [M+H$^+$].

The following compounds were prepared from 6-bromo-3-(2-methoxyphenyl)-[1,2,4]triazolo[4,3-a]pyridine and the corresponding phenylboronic acid using a procedure similar to those described for the synthesis of Example 22.

Example 23

3-(2-Methoxyphenyl)-6-(3-methylphenyl)-[1,2,4]triazolo[4,3-a]pyridine $^1$H NMR (DMSO-$d_6$): 8.11 (m, 1H), 7.93 (dd, J=9.6 and 0.9 Hz, 1H), 7.77 (d, J=9.6 and 1.8 Hz, 1H), 7.63 (m, 2H), 7.51-7.47 (m, 2H), 7.40-7.31 (m, 2H), 7.25-7.17 (m, 2H), 3.86 (s, 3H), 2.37 (s, 3H). MS: m/z 316.2 [M+H$^+$].

Example 24

3-(2-Methoxyphenyl)-6-phenyl-[1,2,4]triazolo[4,3-a]pyridine $^1$H NMR (DMSO-d$_6$): 8.14 (m, 1H), 7.95 (dd, J=9.6 and 1.2 Hz, 1H), 7.79 (dd, J=9.6 and 1.8 Hz, 1H), 7.72-7.62 (m, 4H), 7.52-7.42 (m, 3H), 7.32 (d, J=7.8 Hz, 1H), 7.17 (t, J=8.0 Hz, 1H), 3.86 (s, 3H). MS: m/z 302.2 [M+H$^+$].

Example 25

6-(2,4-Dimethylphenyl)-3-(2-methoxyphenyl)-[1,2,4]triazolo[4,3-a]pyridine $^1$H NMR (DMSO-d$_6$): 7.88 (dd, J=9.6 and 0.9 Hz, 1H), 7.79 (m, 1H), 7.62-7.59 (m, 2H), 7.43 (dd, J=9.6 and 1.8 Hz, 1H), 7.26 (d, J=8.1 Hz, 1H), 7.19-7.14 (m, 3H), 7.08 (d, J=7.5 Hz, 1H), 3.82 (s, 3H), 2.31 (s, 3H), 2.24 (s, 3H). MS: m/z 330.2 [M+H$^+$].

Example 26

6-(3-Chloro-4-methoxyphenyl)-3-(2-methoxyphenyl)-[1,2,4]triazolo[4,3-a]pyridine $^1$H NMR (DMSO-d$_6$): 8.19 (s, 1H), 7.92 (d, J=9.6 Hz, 1H), 7.82-7.76 (m, 2H), 7.69-7.62 (m, 3H), 7.33-7.17 (m, 3H), 3.90 (s, 3H), 3.84 (s, 3H). MS: m/z 366.1 [M+H$^+$].

Example 27

3-(2-Methoxyphenyl)-6-(4-trifluoromethylphenyl)-[1,2,4]triazolo[4,3-a]pyridine $^1$H NMR (DMSO-d$_6$): 8.31 (s, 1H), 8.01-7.94 (m, 3H), 7.85-7.82 (m, 3H), 7.68-7.63 (m, 2H), 7.32 (d, J=9.0 Hz, 1H), 7.17 (t, J=7.5 Hz, 1H), 3.85 (s, 3H). MS: m/z 370.1 [M+H$^+$].

Example 28

6-(3-Methoxy-4-methylphenyl)-3-(2-methoxyphenyl)-[1,2,4]triazolo[4,3-a]pyridine $^1$H NMR (DMSO-d$_6$): 8.15 (m, 1H), 7.93 (dd, J=9.6 and 0.9 Hz, 1H), 7.80 (dd, J=9.6 and 1.8 Hz, 1H), 7.67-7.61 (m, 2H), 7.32 (d, J=8.1 Hz, 1H), 7.25-7.14 (m, 4H), 3.88 (s, 6H), 2.18 (s, 3H). MS: m/z 346.2 [M+H$^+$].

Example 29

3-(2-Methoxyphenyl)-6-(3,4,5-trimethoxyphenyl)-[1,2,4]triazolo[4,3-a]pyridine $^1$H NMR (DMSO-d$_6$): 8.20 (m, 1H), 7.93 (dd, J=9.6 and 0.9 Hz, 1H), 7.81 (dd, J=9.6 and 1.8 Hz, 1H), 7.67-7.62 (m, 2H), 7.32 (d, J=8.1 Hz, 1H), 7.19 (t, J=7.5 Hz, 1H), 6.93 (s, 2H), 3.92 (s, 3H), 3.87 (s, 6H), 3.69 (s, 3H). MS: m/z 392.2 [M+H$^+$].

Example 30

6-(3,5-Dimethyl-4-methoxyphenyl)-3-(2-methoxyphenyl)-[1,2,4]triazolo[4,3-a]pyridine $^1$H NMR (DMSO-d$_6$): 8.11 (m, 1H), 7.96 (dd, J=9.6 and 0.9 Hz, 1H), 7.79 (dd, J=9.6 and 1.8 Hz, 1H), 7.70-7.67 (m, 2H), 7.41-7.36 (m, 3H), 7.25 (t, J=8.0 Hz, 1H), 3.91 (s, 3H), 3.73 (s, 3H), 2.33 (s, 6H). MS: m/z 360.2 [M+H$^+$].

Example 31

6-(3,4-Dimethoxyphenyl)-3-(2-methoxyphenyl)-[1,2,4]triazolo[4,3-a]pyridine $^1$H NMR (DMSO-d$_6$): 8.12 (m, 1H), 7.91 (dd, J=9.6 and 0.9 Hz, 1H), 7.78 (dd, J=9.6 and 1.5 Hz, 1H), 7.66-7.61 (m, 2H), 7.31 (d, J=8.4 Hz, 1H), 7.23-7.16 (m, 3H), 7.05 (d, J=8.4 Hz, 1H), 3.89 (s, 3H), 3.85 (s, 3H), 3.79 (s, 3H). MS: m/z 362.2 [M+H$^+$].

Example 32

6-(3,4-Dimethylphenyl)-3-(2-methoxyphenyl)-[1,2,4]triazolo[4,3-a]pyridine $^1$H NMR (DMSO-d$_6$): 8.07 (m, 1H), 7.92 (dd, J=9.6 and 0.9 Hz, 1H), 7.75 (dd, J=9.6 and 1.8 Hz, 1H), 7.64-7.62 (m, 2H), 7.47 (s, 1H), 7.40 (d, J=8.0 Hz, 1H), 7.31 (d, J=8.1 Hz, 1H), 7.24-7.16 (m, 2H), 3.85 (s, 3H), 2.27 (s, 3H), 2.25 (s, 3H). MS: m/z 330.2 [M+H$^+$].

Example 33

6-(3-Fluoro-4-methylphenyl)-3-(2-methoxyphenyl)-[1,2,4]triazolo[4,3-a]pyridine $^1$H NMR (DMSO-d$_6$): 8.22 (m, 1H), 7.93 (dd, J=9.6 and 1.2 Hz, 1H), 7.79 (dd, J=9.6 and 1.5 Hz, 1H), 7.67-7.30 (m, 6H), 7.19 (t, J=7.5 Hz, 1H), 3.84 (s, 3H), 2.27 (s, 3H). MS: m/z 334.2 [M+H$^+$].

Example 34

6-(4-Hexyloxyphenyl)-3-(2-methoxyphenyl)-[1,2,4]triazolo[4,3-a]pyridine $^1$H NMR (DMSO-d$_6$): 8.04 (m, 1H), 7.91 (dd, J=9.6 and 0.9 Hz, 1H), 7.75 (dd, J=9.6 and 1.5 Hz, 1H), 7.63-7.60 (m, 4H), 7.31 (d, J=8.4 Hz, 1H), 7.19 (t, J=7.2 Hz, 1H), 7.02 (d, J=8.7 Hz, 2H), 4.00 (t, J=6.6 Hz, 2H), 3.85 (s, 3H), 1.76-1.67 (m, 2H), 1.44-1.28 (m, 6H), 0.88 (t, J=6.9 Hz, 3H). MS: m/z 402.2 [M+H$^+$].

Example 35

6-(3-Fluoro-4-methoxyphenyl)-3-(2-methoxyphenyl)-[1,2,4]triazolo[4,3-a]pyridine $^1$H NMR (DMSO-d$_6$): 8.18 (m, 1H), 7.92 (dd, J=9.6 and 0.9 Hz, 1H), 7.78 (dd, J=9.6 and 1.8 Hz, 1H), 7.68-7.62 (m, 3H), 7.52 (m, 1H), 7.32-7.16 (m, 3H), 3.88 (s, 3H), 3.84 (s, 3H). MS: m/z 350.2 [M+H$^+$].

Example 36

6-(2,4-Dimethoxyphenyl)-3-(2-methoxyphenyl)-[1,2,4]triazolo[4,3-a]pyridine $^1$H NMR (DMSO-d$_6$): 7.88-7.19 (m, 2H), 7.66-7.53 (m, 3H), 7.30 (d, J=8.4 Hz, 2H), 7.18 (t, J=7.5 Hz, 1H), 6.70 (d, J=2.4 Hz, 1H), 6.62 (dd, J=8.4 and 2.4 Hz, 1H), 3.84 (s, 3H), 3.81 (s, 3H), 3.79 (s, 3H). MS: m/z 362.2 [M+H$^+$].

Example 37

6-(4-Benzyloxy-3-methylphenyl)-3-(2-methoxyphenyl)-[1,2,4]triazolo[4,3-a]pyridine $^1$H NMR (DMSO-$d_6$): 8.05 (s, 1H), 7.90 (d, J=9.6 Hz, 1H), 7.75 (d, J=9.6 Hz, 1H), 7.64-7.61 (m, 2H), 7.52-7.30 (m, 8H), 7.19 (t, J=8.1 Hz, 1H), 7.10 (d, J=8.4 Hz, 1H), 5.18 (s, 2H), 3.86 (s, 3H), 2.27 (s, 3H). MS: m/z 422.2 [M+H$^+$].

Example 38

6-(4-Ethoxyphenyl)-3-(2-methoxyphenyl)-[1,2,4]triazolo[4,3-a]pyridine $^1$H NMR (DMSO-$d_6$): 8.05 (m, 1H), 7.91 (dd, J=9.6 and 1.2 Hz, 1H), 7.76 (dd, J=9.6 and 1.8 Hz, 1H), 7.67-7.61 (m, 4H), 7.32 (d, J=8.1 Hz, 1H), 7.19 (t, J=7.5 Hz, 1H), 7.02 (d, J=8.7 Hz, 2H), 4.06 (q, J=6.9 Hz, 2H), 3.85 (s, 3H), 1.34 (t, J=6.9 Hz, 3H). MS: m/z 346.2 [M+H$^+$].

Example 39

3-(2-Methoxyphenyl)-6-(4-nitrophenyl)-[1,2,4]triazolo[4,3-a]pyridine $^1$H NMR (DMSO-$d_6$): 8.40 (s, 1H), 8.32-8.30 (m, 2H), 8.04-7.86 (m, 4H), 7.66-7.63 (m, 2H), 7.34-7.17 (m, 2H), 3.85 (s, 3H). MS: m/z 347.1 [M+H$^+$].

Example 40

6-(4-Methoxy-3-nitrophenyl)-3-(2-methoxyphenyl)-[1,2,4]triazolo[4,3-a]pyridine $^1$H NMR (DMSO-$d_6$): 8.37 (m, 1H), 8.31 (m, 1H), 8.09 (dd, J=9.0 and 2.4 Hz, 1H), 8.02 (d, J=9.6 Hz, 1H), 7.88 (dd, J=9.6 and 1.8 Hz, 1H), 7.71-7.69 (m, 2H), 7.52 (d, J=8.7 Hz, 1H), 7.38 (d, J=8.7 Hz, 1H), 7.26 (t, J=7.5 Hz, 1H), 4.03 (s, 3H), 3.91 (s, 3H). MS: m/z 377.1 [M+H$^+$].

Example 41

6-(4-Hydroxy-3-methylphenyl)-3-(2-methoxyphenyl)-[1,2,4]triazolo[4,3-a]pyridine $^1$H NMR (DMSO-$d_6$): 9.58 (s, 1H), 7.96 (s, 1H), 7.88 (d, J=9.6 Hz, 1H), 7.72 (d, J=9.6 Hz, 1H), 7.67-7.60 (m, 2H), 7.40 (s, 1H), 7.35 (d, J=8.1 Hz, 2H), 7.19 (t, J=7.5 Hz, 1H), 6.86 (d, J=5.2 Hz, 1H), 3.85 (s, 3H), 2.17 (s, 3H). MS: m/z 332.2 [M+H$^+$].

Example 42

6-(4-Methoxy-3-nitrophenyl)-3-(2-methoxy-5-nitrophenyl)-[1,2,4]triazolo[4,3-a]pyridine To a flask charged with 3-(2-methoxyphenyl)-6-(4-methoxyphenyl)-[1,2,4]triazolo[4,3-a]pyridine (100 mg, 0.3 mmol) and concentrated sulfuric acid (H$_2$SO$_4$, 5 mL) kept in ice salt bath (−15° C.) was added nitric acid (HNO$_3$, 20 mg, 0.3 mmol), and it was stirred at −15° C. for 1 h. The reaction mixture was added to about 30 g of ice, and adjusted to pH=9 with solid NaHCO$_3$. The mixture was filtered and the solids were washed with methanol (10 mL×3), dried to give the title compound (50 mg, 37% yield) as yellow solids. $^1$H NMR (DMSO-$d_6$): 8.56-8.47 (m, 3H), 8.25 (m, 1H), 7.98-8.07 (m, 2H), 7.87 (dd, J=9.3 and 1.2 Hz, 1H), 7.55 (d, J=9.3 Hz, 1H), 7.47 (d, J=8.7 Hz, 1H), 3.99 (s, 3H), 3.97 (s, 3H). MS: m/z 422.1 [M+H$^+$].

Example 43

6-(4-Amino-3-methoxyphenyl)-3-(2-methoxyphenyl)-[1,2,4]triazolo[4,3-a]pyridine

A flask was charged with 6-(3-methoxy-4-nitrophenyl)-3-(2-methoxyphenyl)-[1,2,4]triazolo[4,3-a]pyridine (100 mg, 0.27 mmol), stannous chloride dihydrate (SnCl$_2$, 300 mg, 1.35 mmol) and MeOH (10 mL). The mixture was stirred at 50° C. under Argon for 4 h. The pH of the mixture was adjusted to around 9 by progressively adding solid NaHCO$_3$, and it was evaporated to afford the crude product. The crude product was purified by column chromatography on silica gel (petroleum ether:ethyl acetate=1:1) to give the title compound (28.5 mg, 31.2% yield) as yellow solids. $^1$H NMR (DMSO-$d_6$): 7.99 (s, 1H), 7.87 (d, J=9.6 Hz, 1H), 7.75 (d, J=9.6 Hz, 1H), 7.67-7.61 (m, 2H), 7.32 (d, J=8.4 Hz, 1H), 7.19 (t, J=7.5 Hz, 1H), 7.07 (d, J=1.8 Hz, 1H), 7.02 (dd, J=8.1 and 1.8 Hz, 1H), 6.71 (d, J=8.1 Hz, 1H), 5.00 (s, 2H), 3.89 (s, 3H), 3.85 (s, 3H). MS: m/z 347.2 [M+H$^+$].

Example 44 was prepared from 3-(2-methoxyphenyl)-6-(4-methyl-3-nitrophenyl)-[1,2,4]triazolo[4,3-a]pyridine using a procedure similar to those described for the synthesis of Example 43.

Example 44

6-(3-Amino-4-methylphenyl)-3-(2-methoxyphenyl)-[1,2,4]triazolo[4,3-a]pyridine $^1$H NMR (DMSO-$d_6$): 7.90-7.89 (m, 2H), 7.61-7.69 (m, 3H), 7.33 (d, J=8.1 Hz, 1H), 7.21 (t, J=7.5 Hz, 1H), 7.02 (d, J=8.4 Hz, 1H), 6.86 (d, J=1.8 Hz, 1H), 6.77 (dd, J=7.5 and 1.8 Hz, 1H), 5.01 (s, 2H), 3.86 (s, 3H), 2.08 (s, 3H). MS: m/z 331.2 [M+H$^+$].

Example 45

6-(3-Aminophenyl)-3-(2-methoxyphenyl)-[1,2,4]triazolo[4,3-a]pyridine hydrochloride a) 6-(3-(tert-Butoxycarbonylamino)phenyl)-3-(2-methoxyphenyl)-[1,2,4]triazolo[4,3-a]pyridine The title compound was prepared from 6-bromo-3-(2-methoxyphenyl)-[1,2,4]triazolo[4,3-a]pyridine and 3-(tert-butoxycarbonylamino)phenylboronic acid using a procedure similar to those described for the synthesis of Example 22, and was isolated as yellow solids (78 mg, 22.0% yield). MS: m/z 417.2 [M+H$^+$].

b) 6-(3-Aminophenyl)-3-(2-methoxyphenyl)-[1,2,4]triazolo[4,3-a]pyridine hydrochloride A mixture of 6-(3-(tert-butoxycarbonylamino)phenyl)-3-(2-methoxyphenyl)-[1,2,4]triazolo[4,3-a]pyridine (78 mg, 0.19 mmol) in HCl/ethyl acetate (2M, 20 mL) was stirred at room temperature for about 3 h. The mixture was concentrated under reduced pressure to give the crude compound. It was recrystallized in MeOH/ethyl acetate to give the title compound (9.8 mg, 15% yield) as yellow solids. $^1$H NMR (DMSO-$d_6$): 8.36 (s, 1H), 8.16 (d, J=8.1 Hz, 1H), 8.05 (d, J=8.1 Hz, 1H), 7.78-7.60 (m, 5H), 7.49 (d, J=6.9 Hz, 1H), 7.37 (d, J=7.8 Hz, 1H), 7.23 (t, J=6.6 Hz, 1H), 3.92 (s, 3H). MS: m/z 317.2 [M+H$^+$].

Example 46

6-(3-Amino-4-methoxyphenyl)-3-(2-methoxyphenyl)-[1,2,4]triazolo[4,3-a]pyridine hydrochloride A mixture of 6-(4-methoxy-3-nitrophenyl)-3-(2-methoxyphenyl)-[1,2,4]triazolo[4,3-a]pyridine (80 mg, 0.21 mmol), iron (59 mg, 1.06 mmol) and NH$_4$Cl (6 mg, 0.11 mmol) in ethanol (10 mL) and water (10 ml) was stirred for 3 h at 70° C. The mixture was concentrated under reduced pressure at 50° C. to remove ethanol, and was extracted with ethyl acetate (40 mL×4). The combined organic phase were dried over anhydrous Na$_2$SO$_4$ and filtered. The filtrate was concentrated under reduced pressure to give a product. The product was dissolved in HCl/ethyl acetate (2M, 20 mL), stirred at room temperature for 30 min, and concentrated to dryness to give the title compound (7.45 mg, 10.2% yield) as yellow solids. $^1$H NMR (DMSO-d$_6$): 8.14 (m, 1H), 8.05 (dd, J=9.6 and 0.9 Hz, 1H), 7.88 (dd, J=9.6 and 1.5 Hz, 1H), 7.71-7.58 (m, 4H), 7.35 (d, J=8.1 Hz, 1H), 7.26-7.19 (m, 2H), 3.92 (s, 3H), 3.89 (s, 3H). MS: m/z 347.2 [M+H$^+$].

Example 47 was prepared from 3-(2-methoxyphenyl)-6-(4-nitrophenyl)-[1,2,4]triazolo[4,3-a]pyridine using a procedure similar to those described for the synthesis of Example 46.

Example 47

6-(4-Aminophenyl)-3-(2-methoxyphenyl)-[1,2,4]triazolo[4,3-a]pyridine hydrochloride $^1$H NMR (DMSO-d$_6$): 8.44 (s, 1H), 8.14 (s, 2H), 7.84 (d, J=8.7 Hz, 2H), 7.74-7.65 (m, 2H), 7.46 (d, J=8.7 Hz, 2H), 7.36 (d, J=8.1 Hz, 1H), 7.23 (t, J=7.2 Hz, 1H), 3.88 (s, 3H). MS: m/z 317.2 [M+H$^+$].

Example 48

6-(4-Methylaminophenyl)-3-(2-methoxyphenyl)-[1,2,4]triazolo[4,3-a]pyridine hydrochloride a) 6-(4-(t-Butylcarbonylamino)phenyl)-3-(2-methoxyphenyl)-[1,2,4]triazolo[4,3-a]pyridine A mixture of 6-(4-aminophenyl)-3-(2-methoxyphenyl)-[1,2,4]triazolo[4,3-a]pyridine (110 mg, 0.31 mmol), di-tert-butyldicarbonate (126 mg, 1.25 mmol) and triethylamine in DCM (40 mL) was stirred at room temperature overnight. The mixture was washed with water and extracted with ethyl acetate (100 mL×4). The combined organic phase were dried over anhydrous Na$_2$SO$_4$ and filtered. The filtrate was concentrated under reduced pressure to give the title compound (120 mg, 93.0% yield) as yellow solids. MS: m/z 417.2 [M+H$^+$].

b) 6-(4-(N-Methyl-t-butylcarbonylamino)phenyl)-3-(2-methoxyphenyl)-[1,2,4]triazolo[4,3-a]pyridine To a mixture of 6-(4-t-butylcarbonylaminophenyl)-3-(2-methoxyphenyl)-[1,2,4]triazolo[4,3-a]pyridine (120 mg, 0.29 mmol) in dry THF (20 mL) cooled at 0° C. was added NaH (12 mg, 0.32 mmol), and it was stirred for 2 h. To the mixture was added iodomethane (164 mg, 1.5 mmol) in THF (8 mL) dropwise, and the mixture was stirred at room temperature overnight. The reaction mixture was quenched with saturated NH$_4$Cl (20 mL) and extracted with ethyl acetate (100 mL×3). The combined organic phase was dried over anhydrous Na$_2$SO$_4$ and filtered. The filtrate was concentrated and the residue was purified by preparative TLC to give the title compound (38 mg, 31% yield) as yellow solids. MS: m/z 431.3 [M+H$^+$].

c) 6-(4-Methylaminophenyl)-3-(2-methoxyphenyl)-[1,2,4]triazolo[4,3-a]pyridine hydrochloride The title compound was prepared from 6-(4-(N-methyl-t-butylcarbonylamino)phenyl)-3-(2-methoxyphenyl)-[1,2,4]triazolo[4,3-a]pyridine using a procedure similar to those described for the synthesis of Example 45b, and was isolated as yellow solids. $^1$H NMR (DMSO-d$_6$): 8.34 (s, 1H), 8.18-8.09 (m, 2H), 7.73-7.65 (m, 4H), 7.36 (d, J=8.4 Hz, 1H), 7.26-7.13 (m, 3H), 3.88 (s, 3H), 2.82 (s, 3H). MS: m/z 331.1 [M+H$^+$].

Example 49

3-(4-Chloro-2-methoxyphenyl)-6-(3-fluoro-4-methoxyphenyl)-[1,2,4]triazolo[4,3-a]pyridine a) 6-Chloro-3-(4-chloro-2-methoxyphenyl)-[1,2,4]triazolo[4,3-a]pyridine The title compound was prepared from 2,5-dichloropyridine and 2-methoxy-4-chlorobenzoic acid using procedures similar to those described for the synthesis of Examples 1a-1c, and was isolated as yellow solids. $^1$H NMR (DMSO-d$_6$): 8.37 (s, 1H), 7.92 (dd, J=9.6 Hz, J=0.9 Hz, 1H), 7.60 (d, J=8.4 Hz, 1H), 7.49 (dd, J=9.6 Hz, J=1.8 Hz, 1H), 7.39 (s, 1H), 7.24 (dd, J=8.1 Hz, J=1.8 Hz, 1H), 3.86 (s, 3H). MS: m/z 294.0 [M+H$^+$].

b) 3-(4-Chloro-2-methoxyphenyl)-6-(3-fluoro-4-methoxyphenyl)-[1,2,4]triazolo[4,3-a]pyridine The title compound was prepared form 6-chloro-3-(4-chloro-2-methoxyphenyl)-[1,2,4]triazolo[4,3-a]pyridine and 3-fluoro-4-methoxyphenylboronic acid using a procedure similar to those described for the synthesis of Example 1d, and was isolated as white solids. $^1$H NMR (DMSO-d$_6$): 8.29 (m, 1H), 7.92 (dd, J=9.6 and 0.9 Hz, 1H), 7.80 (dd, J=9.6 and 1.8 Hz, 1H), 7.71-7.62 (m, 2H), 7.56 (m, 1H), 7.54 (t, J=1.2 Hz, 1H), 7.40-7.23 (m, 2H), 3.88 (s, 3H), 3.87 (s, 3H). MS: m/z 384.2 [M+H$^+$].

Example 50 was prepared from 6-chloro-3-(4-chloro-2-methoxyphenyl)-[1,2,4]triazolo[4,3-a]pyridine and 2-methoxy-5-(4,4,5,5-tetramethyl-1,3,2-dioxaborolan-2-yl)aniline using a procedure similar to those described for the synthesis of Example 22.

Example 50

6-(3-Amino-4-methoxyphenyl)-3-(4-chloro-2-methoxyphenyl)-[1,2,4]triazolo[4,3-a]pyridine $^1$H NMR (CD$_3$OD): 7.94 (s, 1H), 7.83-7.76 (m, 2H), 7.61 (d, J=8.4 Hz, 1H), 7.34 (s, 1H), 7.24 (d, J=6.6 Hz, 1H), 6.99-6.90 (m, 3H), 4.09 (s, 3H), 3.88 (s, 3H). MS: m/z 381.1 [M+H$^+$].

Example 51

6-(3-Hydroxy-4-methoxyphenyl)-3-(2-methoxy-4-methylphenyl)-[1,2,4]triazolo[4,3-a]pyridine a) 6-Chloro-3-(2-methoxy-4-methylphenyl)-[1,2,4]triazolo[4,3-a]pyridine The title compound was prepared from 2,5-dichloropyridine and 2-methoxy-4-methylbenzoic acid using procedures similar to those described for the synthesis of Examples 1a-1c, and was isolated as yellow solids. MS: m/z 274.1 [M+H$^+$].

b) 6-(3-Hydroxy-4-methoxyphenyl)-3-(2-methoxy-4-methylphenyl)-[1,2,4]triazolo[4,3-a]pyridine The title compound was prepared from 6-chloro-3-(2-methoxy-4-methylphenyl)-[1,2,4]triazolo[4,3-a]pyridine and 2-methoxy-5-(4,4,5,5-tetramethyl-1,3,2-dioxaborolan-2-yl)phenol using a procedure similar to those described for the synthesis of Example 1d, and was isolated as yellow solids. $^1$H NMR (DMSO-d$_6$): 9.23 (s, 1H), 7.91-7.86 (m, 2H), 7.69 (dd, J=9.6 and 1.5 Hz, 1H), 7.49 (d, J=7.5 Hz, 1H), 7.16-6.99 (m, 5H), 3.84 (s, 3H), 3.80 (s, 3H), 2.45 (s, 3H). MS: m/z 362.2 [M+H$^+$].

The following compounds were prepared from 6-chloro-3-(2-methoxy-4-methylphenyl)-[1,2,4]triazolo[4,3-a]pyridine and the corresponding substituted phenylboronic acid using a procedure similar to those described for the synthesis of Example 1d.

Example 52

6-(3-Amino-4-methoxyphenyl)-3-(2-methoxy-4-methylphenyl)-[1,2,4]triazolo[4,3-a]pyridine $^1$H NMR (CD$_3$OD): 7.80 (s, 1H), 7.71 (d, J=9.3 Hz, 1H), 7.64 (d, J=9.3 Hz, 1H), 7.43 (d, J=7.8 Hz, 1H), 7.06 (s, 1H), 6.96 (d, J=7.8 Hz, 1H), 6.90 (s, 1H), 6.81 (s, 2H), 3.83 (s, 3H), 3.81 (s, 3H), 2.45 (s, 3H). MS: m/z 361.2 [M+H$^+$].

Example 53

6-(3-Fluoro-4-methoxyphenyl)-3-(2-methoxy-4-methylphenyl)-[1,2,4]triazolo[4,3-a]pyridine $^1$H NMR (DMSO-d$_6$): 8.11 (s, 1H), 7.86 (d, J=9.0 Hz, 1H), 7.74 (dd, J=9.6 and 1.5 Hz, 1H), 7.62 (dd, J=12.9 and 2.1 Hz, 1H), 7.50-7.43 (m, 2H), 7.23 (t, J=9.0 Hz, 1H), 7.11 (s, 1H), 6.98 (d, J=7.5 Hz, 1H), 3.85 (s, 3H), 3.80 (s, 3H), 2.43 (s, 3H). MS: m/z 364.2 [M+H$^+$].

Example 54

3-(2-Methoxyphenyl)-6-(4-methoxyphenyl)-7-methyl-[1,2,4]triazolo[4,3-a]pyridine The title compound was prepared from 2,5-dibromo-4-methylpyridine, 2-methoxybenzoic acid and 4-methoxyphenylboronic acid using procedures similar to those described for the synthesis of Examples 1a-1d, and was isolated as yellow solids. $^1$H NMR (DMSO-d$_6$): 7.75 (s, 1H), 7.64-7.57 (m, 3H), 7.34 (d, J=8.7 Hz, 2H), 7.25 (d, J=7.8 Hz, 1H), 7.16 (t, J=7.2 Hz, 1H), 7.02 (d, J=8.7 Hz, 2H), 3.82 (s, 3H), 3.79 (s, 3H), 2.26 (s, 3H). MS: m/z 346.2 [M+H$^+$].

Example 55

3-(2-Methoxyphenyl)-6-(4-methoxyphenyl)-8-methyl-[1,2,4]triazolo[4,3-a]pyridine The title compound was prepared from 2,5-dibromo-3-methylpyridine, 2-methoxybenzoic acid and 4-methoxyphenylboronic acid using procedures similar to those described for the synthesis of Examples 1a-1d, and was isolated as yellow solids. $^1$H NMR (DMSO-d$_6$): 7.90 (s, 1H), 7.67-7.58 (m, 5H), 7.31 (d, J=8.1 Hz, 1H), 7.19 (t, J=6.9 Hz, 1H), 7.03 (d, J=9.0 Hz, 2H), 3.84 (s, 3H), 3.79 (s, 3H), 2.65 (s, 3H). MS: m/z 346.2 [M+H$^+$].

Example 56

6-(4-Hydroxy-3-methoxyphenyl)-3-(2-methoxyphenyl)-[1,2,4]triazolo[4,3-a]pyridine The title compound was prepared from 2,5-dichloropyridine, 2-methoxybenzoic acid and 2-methoxy-4-(4,4,5,5-tetramethyl-1,3,2-dioxaborolan-2-yl)phenol using procedures similar to those described for the synthesis of Examples 1a-1d. $^1$H NMR (DMSO-d$_6$): 9.25 (s, 1H), 8.06 (m, 1H), 7.90 (dd, J=9.6 and 0.6 Hz, 2H), 7.76 (dd, J=9.6 and 1.5 Hz, 2H), 7.66-7.62 (m, 2H), 7.32 (d, J=8.4 Hz, 1H), 7.16-7.22 (m, 2H), 7.07-7.11 (m, 1H), 6.86 (d, J=8.1 Hz, 1H), 3.89 (s, 3H), 3.86 (s, 3H). MS: m/z 348.2 [M+H$^+$].

Example 57

3-(4-Chloro-2-methoxyphenyl)-6-(4-methoxyphenyl)-[1,2,4]triazolo[4,3-a]pyridine a) 2-Chloro-5-(4-methoxyphenyl)pyridine A flask was charged with 4-methoxyphenylboronic acid (1.0 g, 6.8 mmol), 5-bromo-2-chloropyridine (1.0 g, 5.2 mmol), Pd(PPh$_3$)$_4$ (50 mg, 0.043 mmol), potassium carbonate (1.08 g, 7.8 mmol), 1,4-dioxane (40 mL) and water (4 mL). The mixture was stirred at 100° C. under Argon for 20 h, and evaporated to afford a crude product. The crude product was purified by chromatography on silica gel (petroleum ether:ethyl acetate=40:1) to give the title compound (1.0 g, 88% yield) as white solids. MS: m/z 220.0 [M+H$^+$].

b) 2-Hydrazinyl-5-(4-methoxyphenyl)pyridine

A round-bottom flask was charged with 2-chloro-5-(4-methoxyphenyl)pyridine (260 mg, 1.19 mmol) and hydrazine hydrate (4 mL) at room temperature. The reaction mixture was heated at 100° C. for 48 h. It was cooled to room temperature, then was kept in a refrigerator for 3 h. The precipitate was filtered, washed with cold water, and dried to give the title compound as gray solids (200 mg, 78.0% yield). MS: m/z 216.1 [M+H$^+$].

c) 4-Chloro-2-methoxy-N'-(5-(4-methoxyphenyl)pyridin-2-yl)-benzohydrazide

A solution of 2-hydrazinyl-5-(4-methoxyphenyl)pyridine (200 mg, 0.93 mmol), 4-chloro-2-methoxybenzoic acid (210 mg, 1.12 mmol), BOP (500 mg, 1.12 mmol) and NMM (330 mg, 3.27 mmol) in DCM (9 mL) was stirred at room temperature under Nitrogen overnight. The resulting mixture was filtered, and the solid was washed with DCM, dried to give the title compound as white solids (290 mg, 81.2% yield), which was used for the next reaction without further purification. MS: m/z 384.2 [M+H$^+$].

d) 3-(4-Chloro-2-methoxyphenyl)-6-(4-methoxyphenyl)-[1,2,4]triazolo[4,3-a]pyridine A flask was charged with the crude 4-chloro-2-methoxy-N'-(5-(4-methoxyphenyl)pyridin-2-yl)-benzohydrazide and POCl$_3$ (13 mL), and the mixture was stirred at 80-100° C. overnight. The mixture was evaporated and the residue was adjusted to pH=9 with aqueous Na$_2$CO$_3$, then it was extracted with ethyl acetate (50 mL×4). The extract was dried over anhydrous Na$_2$SO$_4$ and the solvent was removed by evaporation. The crude product was purified by chromatography on silica (petroleum ether:ethyl acetate=1:1 to 0:1) to give the title compound as white solids (208 mg, 75.0% yield). $^1$H NMR (DMSO-d$_6$): 8.17 (m, 1H), 7.92 (dd, J=9.6 and 1.2 Hz, 1H), 7.77 (dd, J=9.6 and 1.8 Hz, 1H), 7.68-7.62 (m, 3H), 7.40 (d, J=2.1 Hz, 1H), 7.25 (dd, J=8.1 and 2.1 Hz, 1H), 7.04 (d, J=6.6 Hz, 2H), 3.88 (s, 3H), 3.80 (s, 3H). MS: m/z 366.2 [M+H$^+$].

The following compounds were prepared from 2-hydrazinyl-5-(4-methoxyphenyl)pyridine and the corresponding substituted benzoic acid using procedures similar to those described for the synthesis of Examples 57c-d.

Example 58

3-(4-Fluoro-2-methoxyphenyl)-6-(4-methoxyphenyl)-[1,2,4]triazolo[4,3-a]pyridine $^1$H NMR (DMSO-d$_6$): 8.12 (s, 1H), 7.91 (d, J=9.6 Hz, 1H), 7.76 (d, J=9.6 Hz, 1H), 7.67-7.62 (m, 3H), 7.22 (dd, J=11.3 and 2.1 Hz, 1H), 7.05-7.00 (m, 3H), 3.85 (s, 3H), 3.79 (s, 3H). MS: m/z 350.2 [M+H$^+$].

Example 59

3-(4-Bromo-2-methoxyphenyl)-6-(4-methoxyphenyl)-[1,2,4]triazolo[4,3-a]pyridine $^1$H NMR (DMSO-d$_6$): 8.18 (s, 1H), 7.92 (d, J=9.6 Hz, 1H), 7.77 (d, J=9.6 Hz, 1H), 7.67 (d, J=9.0 Hz, 2H), 7.57-7.51 (m, 2H), 7.39 (dd, J=8.1 and 1.5 Hz, 1H), 7.04 (d, J=9.0 Hz, 2H), 3.88 (s, 3H), 3.80 (s, 3H). MS: m/z 410.1[M+H$^+$].

Example 60

3-(2-Methoxy-4-trifluoromethylphenyl)-6-(4-methoxyphenyl)-[1,2,4]triazolo[4,3-a]pyridine $^1$H NMR (DMSO-d$_6$): 8.27 (m, 1H), 7.95 (dd, J=9.6 and 0.9 Hz, 1H), 7.87-7.82 (m, 2H), 7.69 (d, J=8.7 Hz, 2H), 7.58 (s, 1H), 7.54 (d, J=7.8 Hz, 1H), 7.04 (d, J=9.0 Hz, 2H), 3.95 (s, 3H), 3.80 (s, 3H). MS: m/z 400.2 [M+H$^+$].

Example 61

3-(2,6-Dimethoxyphenyl)-6-(4-methoxyphenyl)-[1,2,4]triazolo[4,3-a]pyridine $^1$H NMR (DMSO-d$_6$): 7.90 (dd, J=9.5 and 1.2 Hz, 1H), 7.84 (m, 1H), 7.73 (dd, J=9.5 and 1.5 Hz, 1H), 7.62-7.57 (m, 3H), 7.02 (d, J=8.7 Hz, 2H), 6.89 (d, J=8.4 Hz, 2H), 3.95 (s, 3H), 3.79 (s, 3H), 3.71 (s, 3H). MS: m/z 362.2 [M+H$^+$].

Example 62

3-(2,5-Dimethoxyphenyl)-6-(4-methoxyphenyl)-[1,2,4]triazolo[4,3-a]pyridine $^1$H NMR (DMSO-d$_6$): 8.04 (s, 1H), 7.91 (d, J=9.0 Hz, 1H), 7.76 (d, J=9.0 Hz, 1H), 7.63 (d, J=9.0 Hz, 2H), 7.23-7.17 (m, 3H), 7.04 (d, J=9.0 Hz, 2H), 3.79-3.78 (m, 9H). MS: m/z 362.2 [M+H$^+$].

Example 63

3-(6-Fluoro-2-methoxyphenyl)-6-(4-methoxyphenyl)-[1,2,4]triazolo[4,3-a]pyridine $^1$H NMR (DMSO-d$_6$): 8.10 (m, 1H), 7.95 (dd, J=9.0 and 0.9 Hz, 1H), 7.79 (dd, J=9.0 and 1.5 Hz, 1H), 7.72-7.64 (m, 3H), 7.17-7.02 (m, 4H), 4.03 (s, 3H), 3.80 (s, 3H). MS: m/z 350.2 [M+H$^+$].

Example 64

3,6-Bis(4-methoxyphenyl)-[1,2,4]triazolo[4,3-a]pyridine $^1$H NMR (DMSO-d$_6$): 8.46 (s, 1H), 7.93-7.89 (m, 3H), 7.75-7.68 (m, 3H), 7.19 (d, J=9.0 Hz, 2H), 7.06 (d, J=8.7 Hz, 2H), 3.87 (s, 3H), 3.81 (s, 3H). MS: m/z 332.2 [M+H$^+$].

Example 65

3-(3-Bromo-2,6-dimethoxyphenyl)-6-(4-methoxyphenyl)-[1,2,4]triazolo[4,3-a]pyridine $^1$H NMR (DMSO-d$_6$): 8.09 (m, 1H), 7.93 (dd, J=9.6 and 0.9 Hz, 1H), 7.88 (d, J=9.0 Hz, 1H), 7.78 (dd, J=9.5 and 1.5 Hz, 1H), 7.65 (d, J=8.7 Hz, 2H), 7.07-7.01 (m, 3H), 3.79 (s, 3H), 3.74 (s, 3H), 3.57 (s, 3H). MS: m/z 440.1, 442.1 [M+H$^+$].

Example 66

3-(2-Methoxy-4-methylphenyl)-6-(4-methoxyphenyl)-[1,2,4]triazolo[4,3-a]pyridine $^1$H NMR (DMSO-d$_6$): 8.03 (m, 1H), 7.90 (dd, J=9.5 and 1.2 Hz, 1H), 7.75 (dd, J=9.6 and 1.5 Hz, 1H), 7.64 (d, J=8.7 Hz, 2H), 7.49 (d, J=7.5 Hz, 1H), 7.15 (s, 1H), 7.05-6.99 (m, 3H), 3.83 (s, 3H), 3.80 (s, 3H), 2.46 (s, 3H). MS: m/z 346.2 [M+H$^+$].

Example 67

6-(4-Methoxyphenyl)-3-(2-trifluoromethoxyphenyl)-[1,2,4]triazolo[4,3-a]pyridine $^1$H NMR (DMSO-d$_6$): 8.27 (s, 1H), 7.99-7.92 (m, 2H), 7.84-7.78 (m, 2H), 7.70-7.65 (m, 4H), 7.05 (d, J=8.7 Hz, 2H), 3.80 (s, 3H). MS: m/z 386.1 [M+H$^+$].

Example 68

6-(4-Methoxyphenyl)-3-phenyl-[1,2,4]triazolo[4,3-a]pyridine $^1$H NMR (DMSO-d$_6$): 8.52 (s, 1H), 8.01-7.92 (m, 3H), 7.77-7.58 (m, 6H), 7.06 (d, J=8.7 Hz, 2H), 3.81 (s, 3H). MS: m/z 302.2 [M+H$^+$].

Example 69

6-(4-Methoxyphenyl)-3-(2,4,5-trimethoxyphenyl)-[1,2,4]triazolo[4,3-a]pyridine $^1$H NMR (DMSO-d$_6$): 8.01 (m, 1H), 7.90 (dd, J=9.6 and 0.9 Hz, 1H), 7.74 (dd, J=9.6 and 1.5 Hz, 1H), 7.64 (d, J=8.7 Hz, 2H), 7.16 (s, 1H), 7.05 (d, J=9.0 Hz, 2H), 6.95 (s, 1H), 3.93 (s, 3H), 3.83 (s, 3H), 3.80 (s, 3H), 3.77 (s, 3H). MS: m/z 392.2 [M+H$^+$].

Example 70

3-(2-Methoxy-4-nitrophenyl)-6-(4-methoxyphenyl)-[1,2,4]triazolo[4,3-a]pyridine $^1$H NMR (DMSO-d$_6$): 8.30 (m, 1H), 8.06-8.03 (m, 2H), 7.98-7.91 (m, 2H), 7.84-7.81 (dd, J=9.3 and 1.5 Hz, 1H), 7.69 (d, J=8.7 Hz, 2H), 7.05 (d, J=9.0 Hz, 2H), 4.00 (s, 3H), 3.80 (s, 3H). MS: m/z 377.1 [M+H$^+$].

Example 71

3-(2,4-Dimethoxyphenyl)-6-(4-methoxyphenyl)-[1,2,4]triazolo[4,3-a]pyridine $^1$H NMR (DMSO-d$_6$): 8.02 (m, 1H), 7.89 (dd, J=9.6 and 0.9 Hz, 1H), 7.73 (dd, J=9.6 and 1.8 Hz, 1H), 7.64 (d, J=8.7 Hz, 2H), 7.53 (d, J=8.4 Hz, 1H), 7.04 (d, J=8.7 Hz, 2H), 6.84 (d, J=2.4 Hz, 1H), 6.77 (dd, J=8.7 and 2.4 Hz, 1H), 3.89 (s, 3H), 3.84 (s, 3H), 3.79 (s, 3H). MS: m/z 362.2 [M+H$^+$].

Example 72

6-(4-Methoxyphenyl)-3-(2,3,4-trimethoxyphenyl)-[1,2,4]triazolo[4,3-a]pyridine $^1$H NMR (DMSO-d$_6$): 8.11 (s, 1H), 7.90 (d, J=9.3 Hz, 1H), 7.75 (dd, J=9.6 and 1.5 Hz, 1H), 7.64 (d, J=9.0 Hz, 2H), 7.34 (d, J=8.7 Hz, 1H), 7.02-7.06 (m, 3H), 3.91 (s, 3H), 3.85 (s, 3H), 3.79 (s, 3H), 3.62 (s, 3H). MS: m/z 363.0 [M+H$^+$].

Example 73

3-(2,3-Dimethoxyphenyl)-6-(4-methoxyphenyl)-[1,2,4]triazolo[4,3-a]pyridine $^1$H NMR (DMSO-d$_6$): 8.08 (m, 1H), 7.92 (dd, J=9.6 and 0.9 Hz, 1H), 7.76 (dd, J=9.6 and 1.8 Hz, 1H), 7.62 (d, J=9.0 Hz, 2H), 7.37-7.27 (m, 2H), 7.21 (dd, J=7.2 and 2.1 Hz, 1H), 7.04 (d, J=9.0 Hz, 2H), 3.91 (s, 3H), 3.79 (s, 3H), 3.53 (s, 3H). MS: m/z 392.2 [M+H$^+$].

Example 74

3-(2-Ethoxyphenyl)-6-(4-methoxyphenyl)-[1,2,4]triazolo[4,3-a]pyridine $^1$H NMR (DMSO-d$_6$): 8.12 (s, 1H), 7.91 (d, J=9.6 Hz, 1H), 7.78 (d, J=9.6 Hz, 1H), 7.68-7.59 (m, 4H), 7.28 (d, J=8.4 Hz, 1H), 7.17 (t, J=7.5 Hz, 1H), 7.05 (d, J=8.7 Hz, 2H), 4.15 (q, J=6.9 Hz, 2H), 3.79 (s, 3H), 1.05 (t, J=6.9 Hz, 3H). MS: m/z 346.2 [M+H$^+$].

Example 75

6-(4-Methoxyphenyl)-3-(2-methoxy-5-sulfamoylphenyl)-[1,2,4]triazolo[4,3-a]pyridine $^1$H NMR (DMSO-d$_6$): 8.22 (m, 1H), 8.07-8.04 (m, 2H), 7.95 (dd, J=9.6 and 0.9 Hz, 1H), 7.80 (dd, J=9.6 and 1.8 Hz, 1H), 7.68 (d, J=8.7 Hz, 2H), 7.48 (d, J=9.3 Hz, 1H), 7.42 (s, 2H), 7.04 (d, J=9.0 Hz, 2H), 3.94 (s, 3H), 3.80 (s, 3H). MS: m/z 411.1 [M+H$^+$].

Example 76

3-(2-Methoxy-5-methylphenyl)-6-(4-methoxyphenyl)-[1,2,4]triazolo[4,3-a]pyridine $^1$H NMR (DMSO-d$_6$): 8.02 (s, 1H), 7.91 (d, J=9.6 Hz, 1H), 7.76 (d, J=9.6 Hz, 1H), 7.64 (d, J=9.0 Hz, 2H), 7.45-7.43 (m, 2H), 7.21 (d, J=8.4 Hz, 1H), 7.04 (d, J=8.7 Hz, 2H), 3.81 (s, 3H), 3.80 (s, 3H), 2.35 (s, 3H). MS: m/z 346.2 [M+H$^+$].

Example 77

3-(3-Methoxyphenyl)-6-(4-methoxyphenyl)-[1,2,4]triazolo[4,3-a]pyridine $^1$H NMR (DMSO-d$_6$): 8.54 (s, 1H), 7.96 (d, J=9.3 Hz, 1H), 7.80 (d, J=9.6 Hz, 1H), 7.70 (d, J=8.7 Hz, 2H), 7.55-7.50 (m, 3H), 7.10-7.19 (m, 1H), 7.07 (d, J=8.7 Hz, 2H), 3.87 (s, 3H), 3.81 (s, 3H). MS: m/z 332.2 [M+H$^+$].

Example 78

6-(4-Methoxyphenyl)-3-(2-methylphenyl)-[1,2,4]triazolo[4,3-a]pyridine $^1$H NMR (DMSO-d$_6$): 8.05 (m, 1H), 7.94 (dd, J=9.6 and 0.9 Hz, 1H), 7.76 (dd, J=9.6 and 1.5 Hz, 1H), 7.64-7.60 (m, 3H), 7.54-7.51 (m, 2H), 7.44 (m, 1H), 7.03 (d, J=8.7 Hz, 2H), 3.79 (s, 3H), 2.24 (s, 3H). MS: m/z 316.2 [M+H$^+$].

Example 79

6-(4-Methoxyphenyl)-3-(2-methylaminophenyl)-[1,2,4]triazolo[4,3-a]pyridine $^1$H NMR (DMSO-d$_6$): 8.09 (s, 1H), 7.93 (d, J=9.6 Hz, 1H), 7.75 (dd, J=9.6 and 1.5 Hz, 1H), 7.62 (d, J=9.0 Hz, 2H), 7.52 (dd, J=7.5 and 1.5 Hz, 1H), 7.42 (t, J=7.8 Hz, 1H), 7.05 (d, J=9.0 Hz, 2H), 6.83-6.77 (m, 2H), 5.92 (m, 1H), 3.80 (s, 3H), 2.75 (d, J=4.8 Hz, 3H). MS: m/z 331.2 [M+H$^+$].

Example 80

3-(2-Dimethylaminophenyl)-6-(4-methoxyphenyl)-[1,2,4]triazolo[4,3-a]pyridine $^1$H NMR (DMSO-d$_6$): 7.94-7.91 (m, 2H), 7.77 (dd, J=9.6 and 1.5 Hz, 1H), 7.61-7.53 (m, 4H), 7.28 (d, J=7.8 Hz, 1H), 7.15 (t, J=7.5 Hz, 1H), 7.04 (d, J=8.7 Hz, 2H), 3.79 (s, 3H), 2.43 (s, 6H). MS: m/z 345.5 [M+H$^+$].

Example 81

6-(3-Amino-4-methoxyphenyl)-3-(4-chloro-2-methoxyphenyl)-[1,2,4]triazolo[4,3-a]pyridine hydrochloride

A solution of 6-(3-amino-4-methoxyphenyl)-3-(4-chloro-2-methoxyphenyl)-[1,2,4]triazolo[4,3-a]pyridine (50 mg, 0.131 mmol) in HCl/ethyl acetate (2M, 20 mL) was stirred at room temperature for 0.5 h. It was concentrated under reduced pressure to give the title compound (56 mg, 94% yield) as gray solids. $^1$H NMR (DMSO-d$_6$): 8.32 (s, 1H), 8.10 (d, J=9.6 Hz, 1H), 7.95 (dd, J=9.6 and 1.5 Hz, 1H), 7.79 (d, J=2.1 Hz, 1H), 7.73 (dd, J=8.7 and 2.1 Hz, 1H), 7.66 (d, J=8.1 Hz, 1H), 7.45 (d, J=1.5 Hz, 1H), 7.32-7.27 (m, 2H), 3.94 (s, 3H), 3.93 (s, 3H). MS: m/z 381.2 [M+H$^+$].

The following salts were prepared from the corresponding free base and HCl/ethyl acetate using a procedure similar to those described for the synthesis of Example 81.

Example 82

6-(3-Amino-4-methoxyphenyl)-3-(2-methoxy-4-methylphenyl)-[1,2,4]triazolo[4,3-a]pyridine hydrochloride

$^1$H NMR (DMSO-d$_6$): 8.11 (s, 1H), 8.04 (d, J=9.3 Hz, 1H), 7.89 (dd, J=9.6 and 1.5 Hz, 1H), 7.58-7.50 (m, 3H), 7.23 (d, J=8.4 Hz, 1H), 7.18 (s, 1H), 7.03 (d, J=7.8 Hz, 1H), 3.92 (s, 3H), 3.86 (s, 3H), 2.46 (s, 3H). MS: m/z 361.2 [M+H$^+$].

Example 83

3-(4-Chloro-2-methoxyphenyl)-6-(4-methoxyphenyl)-[1,2,4]triazolo[4,3-a]pyridine hydrochloride

$^1$H NMR (DMSO-d$_6$): 8.23 (m, 1H), 7.96 (d, J=9.6 Hz, 1H), 7.86 (dd, J=9.6 and 1.5 Hz, 1H), 7.70-7.62 (m, 3H), 7.41 (d, J=1.8 Hz, 1H), 7.26 (dd, J=8.1 and 1.8 Hz, 1H), 7.05 (d, J=8.7 Hz, 2H), 3.88 (s, 3H), 3.80 (s, 3H). MS: m/z 366.2 [M+H$^+$].

Example 84

3-(2-Methoxy-4-methylphenyl)-6-(4-methoxyphenyl)-[1,2,4]triazolo[4,3-a]pyridine hydrochloride

$^1$H NMR (DMSO-d$_6$): 8.21 (s, 1H), 8.05-7.97 (m, 2H), 7.71-7.66 (m, 2H), 7.52 (d, J=7.8 Hz, 1H), 7.18 (s, 1H), 7.07-7.02 (m, 3H), 3.85 (s, 3H), 3.81 (s, 3H), 2.47 (s, 3H). MS: m/z 346.2 [M+H$^+$].

Example 85

3-(2-Chloropyridin-3-yl)-6-(4-methoxyphenyl)-[1,2,4]triazolo[4,3-a]pyridine

The title compound was prepared from 2-hydrazinyl-5-(4-methoxyphenyl)pyridine and 2-methoxynicotinic acid using procedures similar to those described for the synthesis of Examples 57c-d, and was isolated as gray solids (230 mg, 68.2% yield). $^1$H NMR (DMSO-d$_6$): 8.71 (dd, J=4.8 and 1.8 Hz, 1H), 8.44 (s, 1H), 8.26 (dd, J=7.7 and 1.8 Hz, 1H), 7.99 (d, J=9.6 Hz, 1H), 7.84 (m, 1H), 7.72-7.68 (m, 2H), 7.04 (d, J=8.7 Hz, 2H), 3.80 (s, 3H). MS: m/z 337.1 [M+H$^+$].

Example 86

6-(4-Methoxyphenyl)-3-(2-methoxypyridin-3-yl)-[1,2,4]triazolo[4,3-a]pyridine

A mixture of 3-(2-chloropyridin-3-yl)-6-(4-methoxyphenyl)-[1,2,4]triazolo[4,3-a]pyridine (178 mg, 0.53 mmol) and sodium methoxide (518 mg, 9.6 mmol) in methanol (60 mL) was heated to reflux for 16 h under Argon. The reaction mixture was cooled to room temperature and concentrated. The residue was mixed with DCM (60 mL) and water (60 mL), and it was separated and the organic layer was washed with brine (50 mL×2) and concentrated. The residue was stirred at room temperature for 0.5 h in petroleum ether (35 mL) and ethyl acetate (5 mL) and filtered. The solids were dried in vacuo to give the title compound (150 mg, 84.0% yield). $^1$H NMR (DMSO-d$_6$): 8.47 (dd, J=4.8 and 1.8 Hz, 1H), 8.32 (m, 1H), 8.10 (dd, J=7.2 and 1.8 Hz, 1H), 7.94 (dd, J=9.6 and 0.9 Hz, 1H), 7.79 (dd, J=9.6 and 1.5 Hz, 1H), 7.69 (d, J=8.7 Hz, 2H), 7.27 (dd, J=7.5 and 5.1 Hz, 1H), 7.05 (d, J=9.0 Hz, 2H), 3.95 (s, 3H), 3.80 (s, 3H). MS: m/z 333.2 [M+H$^+$].

Example 87

3-(4-Amino-2-methoxyphenyl)-6-(4-methoxyphenyl)-[1,2,4]triazolo[4,3-a]pyridine hydrochloride

A mixture of 3-(2-methoxy-4-nitrophenyl)-6-(4-methoxyphenyl)-[1,2,4]triazolo[4,3-a]pyridine (50 mg, 0.13 mmol) and SnCl$_2$ (120 mg, 0.65 mmol) in ethyl acetate (25 mL) was heated to reflux for 6 h under Argon. The reaction mixture was cooled to room temperature and basified to pH=10 with saturated aqueous Na$_2$CO$_3$. The biphasic solution was separated and the aqueous layer was extracted with ethyl acetate (40 mL). The combined organic layers were washed with brine and concentrated. The residue was purified by flash column chromatography (petroleum ether:ethyl acetate=2:1 to 0:1) to give crude product as yellow oil. The oil was stirred in a solution of HCl in ethyl acetate (2M, 20 mL) at room temperature, and then was mixed with water (30 mL). The aqueous phase was washed with ethyl acetate (30 mL), basified with saturated aqueous Na$_2$CO$_3$ to pH>10 and extracted with ethyl acetate (30 mL). The organic phase was stirred with a solution of HCl in ethyl acetate (2M, 10 mL) at room temperature for 2 h and concentrated in vacuo to give the title compound as yellow solids (16 mg, 30% yield). $^1$H NMR (DMSO-d$_6$): 8.32 (s, 1H), 8.19 (dd, J=9.6 and 1.2 Hz, 1H), 8.09 (d, J=9.6 Hz, 1H), 7.72 (d, J=8.7 Hz, 2H), 7.36 (d, J=8.4 Hz, 1H), 7.08 (d, J=8.7 Hz, 2H), 6.61 (d, J=1.5 Hz, 1H), 6.52 (dd, J=8.4 and 1.5 Hz, 1H), 3.82 (s, 3H), 3.79 (s, 3H). MS: m/z 347.1 [M+H$^+$].

The following compounds were prepared from 6-bromo-3-(4-chloro-2-methoxyphenyl)-[1,2,4]triazolo[4,3-a]pyridine or 6-chloro-3-(4-methyl-2-methoxyphenyl)-[1,2,4]triazolo[4,3-a]pyridine and the corresponding phenylboronic acid using a procedure similar to those described for the synthesis of Example 1d.

Example 88

3-(4-Chloro-2-methoxyphenyl)-6-(4-methylaminophenyl)-[1,2,4]triazolo[4,3-a]pyridine

$^1$H NMR (DMSO-d$_6$): 8.02 (s, 1H), 7.86 (d, J=8.7 Hz, 1H), 7.73 (d, J=8.7 Hz, 1H), 7.61 (d, J=7.8 Hz, 1H), 7.48-7.40 (m,

3H), 7.25 (d, J=6.9 Hz, 1H), 6.61 (d, J=6.9 Hz, 2H), 5.96 (s, 1H), 3.87 (s, 3H), 2.70 (s, 3H). MS: m/z 365.2 [M+H$^+$].

Example 89

3-(4-Chloro-2-methoxyphenyl)-6-(3-hydroxy-4-methoxyphenyl)-[1,2,4]triazolo[4,3-a]pyridine $^1$H NMR (DMSO-d$_6$): 9.21 (s, 1H), 8.06 (m, 1H), 7.90 (dd, J=9.6 and 0.9 Hz, 1H), 7.71 (dd, J=9.6 and 1.5 Hz, 1H), 7.63 (d, J=8.1 Hz, 1H), 7.42 (s, 1H), 7.26 (d, J=8.1 Hz, 1H), 7.14-7.09 (m, 2H), 7.01 (d, J=8.1 Hz, 1H), 3.89 (s, 3H), 3.81 (s, 3H). MS: m/z 382.1 [M+H$^+$].

Example 90

6-(3-Amino-4-methylphenyl)-3-(4-chloro-2-methoxyphenyl)-[1,2,4]triazolo[4,3-a]pyridine $^1$H NMR (DMSO-d$_6$): 7.99 (m, 1H), 7.91 (dd, J=9.3 and 0.6 Hz, 1H), 7.70-7.62 (m, 2H), 7.42 (s, 1H), 7.27 (dd, J=8.1 and 2.1 Hz, 1H), 7.02 (d, J=7.8 Hz, 1H), 6.88 (s, 1H), 6.80 (dd, J=7.8 and 1.8 Hz, 1H), 5.01 (s, 2H), 3.89 (s, 3H), 2.08 (s, 3H). MS: m/z 365.1 [M+H$^+$].

Example 91

6-(3-Amino-4-methylphenyl)-3-(4-methyl-2-methoxyphenyl)-[1,2,4]triazolo[4,3-a]pyridine $^1$H NMR (DMSO-d$_6$): 7.91-7.87 (m, 2H), 7.67 (d, J=7.8 Hz, 1H), 7.48 (d, J=7.8 Hz, 1H), 7.16 (s, 1H), 7.02 (d, J=7.8 Hz, 2H), 6.85 (s, 1H), 6.81-6.78 (m, 1H), 5.02 (s, 2H), 3.83 (s, 3H), 2.45 (s, 3H), 2.07 (s, 3H). MS: m/z 345.2 [M+H$^+$].

Example 92

6-(4-Methylaminophenyl)-3-(4-methyl-2-methoxyphenyl)-[1,2,4]triazolo[4,3-a]pyridine $^1$H NMR (CD$_3$OD): 7.88 (m, 1H), 7.79 (m, 2H), 7.51 (d, J=7.8 Hz, 1H), 7.39 (d, J=6.6 Hz, 2H), 7.13 (s, 1H), 7.03 (d, J=7.8 Hz, 1H), 6.69 (d, J=6.6 Hz, 2H), 3.87 (s, 3H), 2.80 (s, 3H), 2.50 (s, 3H). MS: m/z 345.2 [M+H$^+$].

Example 93

Identification of 3-(2-methoxyphenyl)-6-(4-methoxyphenyl)-[1,2,4]triazolo[4,3-a]pyridine and analogs as inhibitors of cell proliferation that were evaluated with standard MTT cancer cell cytotoxicity assay (IC$_{50}$)

Human lung cancer cell line A549, breast cancer cell line T47D, liver cancer cell lines HepG2 and SMMC7721 as well as a mouse melanoma cell line B16F10 were used in the study. The cells were cultured in corresponding growth media recommended by American Type Culture Collection (ATCC) with the supplementation of penicillin G (100 U/ml)/streptomycin (100 lg/ml), and 10% fetal bovine serum (Hangzhou Sijiqing Biological Engineering Materials, Co., Ltd. China) at 37° C. in a humidified atmosphere containing 5% CO$_2$. Cells at about 80% confluency were harvested by trypsinization. Cells were centrifuged, re-suspended in fresh growth media and counted. Corresponding numbers of cells were seeded to 96-well cell culture plates (HepG2 cell, T-47D and A549 cells at 3000 cells/well, SMMC-7721 cells at 5000 cells/well and B16F10 cells at 2000 cells/well) in a total volume of 100 al. Cells were incubated in CO$_2$ incubator over night to allow the cells to attach. In next day, 1001 of medium containing testing (from 10 μM to 1 nM) or reference compounds was added to each well of the cells. Media without compound were used as 100% control. Cells were treated with each concentration of compounds in triplicates to ensure data accuracy. Cells were incubated with compounds in CO$_2$ incubator for an additional 48-72 h at 37° C. After incubation, cells were removed from the CO$_2$ incubator and 201 of 5 mg/ml MTT (3-(4,5-dimethylthiazole-2-yl)-2,5-diphenyltetrazoliumbromide, Sigma) solution in PBS was added to each well. Cells were returned to CO$_2$ incubator and incubated for additional 4 h. After the incubation, media were removed by aspiration and 1001 DMSO was added to each well. Plates were sealed with aluminum foil and shaked mildly on an orbital shaker for 10 min at room temperature. The absorption was measured at 550 nm with a plate reader (Varioskan Flash, Thermo Fisher Scientific) with 660 nm reading used as background control. The relative absorbance readings were calculated by subtracting readings at 660 nm from that at 550 nm. The relative absorbance was plotted again the concentrations of the testing compounds and the plots were fitted with a one-site lg(IC$_{50}$) equation using Prism 5 software (GraphPad Software, Inc). The equation used in the curve fitting is as follows: relative absorbance reading=background reading+ (maximal reading−brackground reading)/(1+10^(compound concentration-log IC$_{50}$)). The background reading used in the calculation was obtained with 100% cell death using a reference anticancer drug, whereas the maximal reading was obtained in the well with no added compound. The IC$_{50}$ value calculated from the equation represents the cytotoxic potency of a particular compound.

The IC$_{50}$ values (nM) are summarized in Table I.

TABLE I

IC$_{50}$ in cancer cells

| Example # | IC$_{50}$ (nM) | | | |
|---|---|---|---|---|
| | A549 | HepG2 | SMMC7721 | T47D |
| 1 | 35 | 28 | 13 | 37 |
| 2 | 252 | 189 | 79 | 184 |
| 3 | >10000 | >10000 | >10000 | >10000 |
| 4 | 276 | 246 | 80 | 326 |
| 5 | 11 | 32 | 11 | 40 |
| 6 | 1060 | 1163 | 535 | 697 |
| 7 | 217 | 136 | 59 | 158 |
| 8 | 91 | 55 | 24 | 103 |
| 9 | >10000 | >10000 | >10000 | >10000 |
| 10 | >10000 | 382 | 618 | 1370 |
| 11 | >10000 | 5288 | 2906 | >10000 |
| 12 | 7180 | 2951 | >10000 | >10000 |
| 13 | 2351 | 1285 | 1007 | 660 |
| 14 | 1268 | 797 | 110 | 1437 |
| 15 | 1031 | 1729 | 1107 | 2013 |
| 16 | 160 | 107 | 33 | 152 |

TABLE I-continued

IC$_{50}$ in cancer cells

| Example # | A549 | HepG2 | SMMC7721 | T47D |
|---|---|---|---|---|
| 17 | 29 | 48 | 14 | 65 |
| 18 | >10000 | >10000 | >10000 | >10000 |
| 19 | 221 | 157 | 68 | 169 |
| 20 | 13 | 11 | >10000 | 18 |
| 21 | >10000 | 4250 | >10000 | >10000 |
| 22 | 192 | 224 | 51 | 147 |
| 23 | 215 | 180 | 76 | 134 |
| 24 | >10000 | >10000 | >10000 | >10000 |
| 25 | 725 | 724 | 114 | 415 |
| 26 | 33 | 23 | 12 | 52 |
| 27 | 9630 | 2642 | 2251 | 4259 |
| 28 | 886 | 448 | 178 | 495 |
| 29 | >10000 | >10000 | >10000 | >10000 |
| 30 | >10000 | 2370 | 1756 | 5156 |
| 31 | 241 | 474 | 492 | 765 |
| 32 | 157 | 83 | 39 | 148 |
| 33 | 630 | 772 | 164 | 804 |
| 34 | >10000 | >10000 | >10000 | >10000 |
| 35 | 20 | 19 | 9.9 | 68 |
| 36 | 74 | 78 | 29 | 315 |
| 37 | 7125 | 3559 | 3340 | 9341 |
| 38 | 49 | 80 | 27 | 74 |
| 39 | 2998 | 3253 | 5440 | >10000 |
| 40 | 2659 | 2462 | 72 | 896 |
| 41 | 212 | 155 | 117 | 129 |
| 42 | 489 | 312 | 230 | 279 |
| 43 | >10000 | 1636 | 2204 | 2246 |
| 44 | 54 | 29 | 20 | 48 |
| 45 | 2934 | 1248 | 829 | 678 |
| 46 | 9.4 | 9.9 | 5.7 | 9.7 |
| 47 | 1052 | 717 | 365 | 189 |
| 48 | 26 | 31 | 11 | 18 |
| 49 | 4.9 | 3.3 | 4.6 | 4.5 |
| 50 | 1.7 | 1.4 | 1.3 | 1.1 |
| 51 | 4.0 | 1.1 | >10000 | 1.1 |
| 52 | 2.6 | 2.3 | 1.8 | 2.0 |
| 53 | 7.4 | 5.7 | 8.3 | 6.7 |
| 54 | 428 | 134 | 94 | 151 |
| 55 | 122 | 88 | 58 | 260 |
| 56 | >10000 | 706 | 1817 | 1478 |
| 57 | 3.4 | 3.4 | 6.7 | 4.1 |
| 58 | 59 | 35 | 17 | 54 |
| 59 | 12 | 7.1 | 3.8 | 6.6 |
| 60 | 91 | 41 | 18 | 68 |
| 61 | 2556 | 949 | 258 | 2924 |
| 62 | 142 | 77 | 42 | 156 |
| 63 | 174 | 236 | 36 | 149 |
| 64 | 641 | 568 | 150 | 341 |
| 65 | 2459 | 944 | 199 | 569 |
| 66 | 12 | 15 | 3.7 | 19 |
| 67 | 471 | 910 | 105 | 328 |
| 68 | 7748 | 5031 | 755 | 2944 |
| 69 | 833 | 915 | 307 | 834 |
| 70 | 6.7 | 22 | 9.9 | 13 |
| 71 | 16 | 15 | 8.7 | 22 |
| 72 | >10000 | >10000 | 4138 | 8157 |
| 73 | >10000 | 2350 | 3209 | 5325 |
| 74 | 146 | 141 | 38 | 151 |
| 75 | >10000 | >10000 | >10000 | >10000 |
| 76 | 533 | 283 | 104 | 633 |
| 77 | 4878 | 2211 | 962 | 1954 |
| 78 | 610 | 264 | 109 | 129 |
| 79 | 167 | 122 | 69 | 73 |
| 80 | 118 | 81 | 35 | 62 |
| 85 | >10000 | 3874 | 1894 | 4342 |
| 86 | 41 | 58 | 32 | 40 |
| 87 | 711 | 356 | 175 | 308 |
| 88 | 4.4 | 6.0 | 1.8 | 3.6 |
| 89 | 1.6 | 1.4 | >10000 | 0.84 |
| 90 | 7.1 | 5.4 | 2.3 | 5.5 |
| 91 | 42 | 39 | 13 | 31 |
| 92 | 11 | 23 | 23 | 8.8 |

The IC$_{50}$ values (nM) in B16F10 cells are summarized in Table II.

TABLE II

IC$_{50}$ values (nM) in B16F10 cells

| Example # | | | | | | |
|---|---|---|---|---|---|---|
| 1 | 2 | 3 | 5 | 6 | 7 | 11 |
| IC$_{50}$ (nM) 36 | 152 | >10000 | 37 | 591 | 220 | 4999 |

| Example # | | | | | | |
|---|---|---|---|---|---|---|
| 20 | 24 | 26 | 27 | 34 | 35 | 38 |
| IC$_{50}$ (nM) 18 | >10000 | 23 | 3825 | >10000 | 16 | 129 |

| Example # | | | | | | |
|---|---|---|---|---|---|---|
| 39 | 40 | 46 | 49 | 50 | 51 | 52 |
| IC$_{50}$ (nM) >10000 | >10000 | 3.7 | 4.9 | 1.6 | 2.1 | 2.1 |

| Example # | | | | | | |
|---|---|---|---|---|---|---|
| 53 | 57 | 59 | 60 | 66 | 70 | 88 |
| IC$_{50}$ (nM) 6.2 | 1.6 | 6.1 | 37 | 3.4 | 4.4 | 5.1 |

| Example # | | | |
|---|---|---|---|
| 89 | 90 | 91 | 92 |
| IC$_{50}$ (nM) 1.1 | 4.6 | 23 | 7.7 |

Thus, 3-(2-methoxyphenyl)-6-(4-methoxyphenyl)-[1,2,4]triazolo[4,3-a]pyridine (Example 1) and analogs are identified as potent inhibitors of cell proliferation in several solid tumor cell lines.

Example 94

Identification of 3-(2-methoxyphenyl)-6-(4-methoxyphenyl)-[1,2,4]triazolo[4,3-a]pyridine and analogs as inducers of apoptosis in solid tumor cells Human breast cancer cell line T-47D and lung cancer cell line A549, growing in DMEM/F12+10% FBS media were seeded to a density of 20000 cells/well in 96-well cell culture plate and grew overnight (18-24 h) in CO$_2$ cell culture incubator at 37° C. Next day the medium were removed by aspiration and 180l fresh growth media was added to each well followed by 20l of growth media containing 10× concentration of reference or testing compounds with 10% DMSO. Twenty four hours later, cell culture plates were centrifuged at 1000 g for 5 min and the supernatant was removed by emptying contents into a reservoir. Fifty μl of Lysis Buffer (10 mM Tris, pH7.5, 0.1M NaCl, 1 Mm EDTA, 0.01% Triton X-100) was added to each well and the plates were incubated with gentle agitation on an orbital shaker at 4° C. for 30 min. The plates were then centrifuged at 1000 g for 10 min at 4° C. and 20 μl of the supernatant was transferred from each well to a corresponding well in a black 384-well. Twenty μl of caspase-3 assay buffer (20 mM PIPES, pH7.4, 4 Mm EDTA and 0.2% CHAPS) containing 20 μM fluorogenic caspase-3 substrate ((Ac-DEVD)$_2$-R110, AnaSpec Cat #60304-5) was added to each well. The samples were mixed by agitation and incubated at 37° C. for 3 h. The fluorescent intensity of each well was read on a fluorescent plate reader (Varioskan Flash, Thermo Fisher Scientific) with excitation wavelength at 496 nm and emission wavelength at 520 nm. The activity of compounds on caspase-3 activation was determined by plotting the relative fluorescent unit (RFU) against the testing concentrations of the compounds. The $EC_{50}$ values were determined by fitting the above responding curves into Prism sigmoidal dose-response equation (GraphPad Software, Inc).

The potency ($EC_{50}$) of compounds to induce caspase-3 activation is summarized in Table III.

TABLE III $EC_{50}$ values in T47D and A549 cells

| Example # | $EC_{50}$ (nM) | |
| --- | --- | --- |
|  | T47D | A-549 |
| 1 | 55 | 83 |
| 5 | 76 | 93 |
| 17 | 86 | ND |
| 20 | 16 | ND |
| 26 | 240 | 32 |
| 35 | 228 | 25 |
| 46 | 23 | ND |
| 48 | 74 | ND |
| 49 | 9.3 | ND |
| 50 | 3.5 | ND |
| 51 | 2.8 | ND |
| 52 | 5.4 | ND |
| 53 | 9.1 | ND |
| 57 | 20 | 5.0 |
| 59 | 25 | ND |
| 66 | 62 | 11 |
| 70 | 22 | ND |
| 71 | 117 | ND |
| 89 | 2.3 | ND |

ND, not determined

Thus, 3-(2-methoxyphenyl)-6-(4-methoxyphenyl)-[1,2,4]triazolo[4,3-a]pyridine (Example 1) and analogs are identified as potent apoptosis inducers in human breast cancer cell line T-47D and lung cancer cell line A549.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:
1. A compound of Formula II:

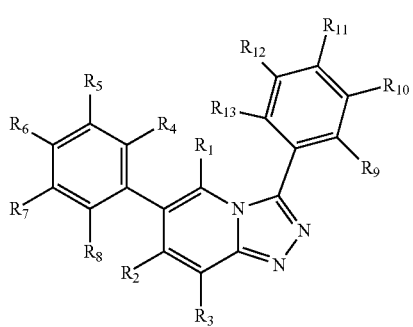

(II)

or a pharmaceutically acceptable salt thereof, wherein:
$R_1$-$R_3$ independently are hydrogen or $C_{1-6}$ alkyl;
$R_4$-$R_{13}$ independently are hydrogen, halo, $C_{1-6}$ alkoxy, $C_{1-10}$ alkyl, halo $C_{1-6}$ alkyl, nitro, hydroxy, primary amino (—$NH_2$), secondary amino (—NHR), tertiary amino (—NRR), or aminosulfonyl; wherein each R is independently $C_{1-6}$ alkyl; with the proviso that at least one $R_4$-$R_{13}$ is independently $C_{1-6}$ alkoxy; or
$R_4$ and $R_5$, or $R_5$ and $R_6$, or $R_6$ and $R_7$, or $R_7$ and $R_8$, taken together with the atoms to which they are attached to form —$OCH_2O$— or —$OCH_2CH_2O$—.

2. The compound of claim 1, wherein said compound is selected from the group consisting of:
3-(2-Methoxyphenyl)-6-(4-methoxyphenyl)-[1,2,4]triazolo[4,3-a]pyridine;
3-(2-Methoxyphenyl)-6-(3-methoxyphenyl)-[1,2,4]triazolo[4,3-a]pyridine;
3,6-Bis(2-methoxyphenyl)-[1,2,4]triazolo[4,3-a]pyridine;
6-(2-Fluoro-4-methylphenyl)-3-(2-methoxyphenyl)-[1,2,4]triazolo[4,3-a]pyridine;
6-(4-Methoxy-3-methylphenyl)-3-(2-methoxyphenyl)-[1,2,4]triazolo[4,3-a]pyridine;
6-(4-Isopropoxyphenyl)-3-(2-methoxyphenyl)-[1,2,4]triazolo[4,3-a]pyridine;
6-(4-Ethylphenyl)-3-(2-methoxyphenyl)-[1,2,4]triazolo[4,3-a]pyridine;
6-(4-Methoxy-2-methylphenyl)-3-(2-methoxyphenyl)-[1,2,4]triazolo[4,3-a]pyridine;
6-(3-Hydroxyphenyl)-3-(2-methoxyphenyl)-[1,2,4]triazolo[4,3-a]pyridine;
6-(4-Hydroxyphenyl)-3-(2-methoxyphenyl)-[1,2,4]triazolo[4,3-a]pyridine;
6-(Benzo[d][1,3]dioxol-5-yl)-3-(2-methoxyphenyl)-[1,2,4]triazolo[4,3-a]pyridine;
6-(4-Ethoxy-3-methylphenyl)-3-(2-methoxyphenyl)-[1,2,4]triazolo[4,3-a]pyridine;
6-(4-Dimethylaminophenyl)-3-(2-methoxyphenyl)-[1,2,4]triazolo[4,3-a]pyridine;
6-(3-Chloro-4-methylphenyl)-3-(2-methoxyphenyl)-[1,2,4]triazolo[4,3-a]pyridine;
6-(3-Hydroxy-4-methoxyphenyl)-3-(2-methoxyphenyl)-[1,2,4]triazolo[4,3-a]pyridine;
3-(2-Methoxyphenyl)-6-(4-methylphenyl)-[1,2,4]triazolo[4,3-a]pyridine;
3-(2-Methoxyphenyl)-6-(3-methylphenyl)-[1,2,4]triazolo[4,3-a]pyridine;
3-(2-Methoxyphenyl)-6-phenyl-[1,2,4]triazolo[4,3-a]pyridine;
6-(2,4-Dimethylphenyl)-3-(2-methoxyphenyl)-[1,2,4]triazolo[4,3-a]pyridine;
6-(3-Chloro-4-methoxyphenyl)-3-(2-methoxyphenyl)-[1,2,4]triazolo[4,3-a]pyridine;
3-(2-Methoxyphenyl)-6-(4-trifluoromethylphenyl)-[1,2,4]triazolo[4,3-a]pyridine;
6-(3-Methoxy-4-methylphenyl)-3-(2-methoxyphenyl)-[1,2,4]triazolo[4,3-a]pyridine;
3-(2-Methoxyphenyl)-6-(3,4,5-trimethoxyphenyl)-[1,2,4]triazolo[4,3-a]pyridine;
6-(3,5-Dimethyl-4-methoxyphenyl)-3-(2-methoxyphenyl)-[1,2,4]triazolo[4,3-a]pyridine;
6-(3,4-Dimethoxyphenyl)-3-(2-methoxyphenyl)-[1,2,4]triazolo[4,3-a]pyridine;
6-(3,4-Dimethylphenyl)-3-(2-methoxyphenyl)-[1,2,4]triazolo[4,3-a]pyridine;
6-(3-Fluoro-4-methylphenyl)-3-(2-methoxyphenyl)-[1,2,4]triazolo[4,3-a]pyridine;
6-(4-Hexyloxyphenyl)-3-(2-methoxyphenyl)-[1,2,4]triazolo[4,3-a]pyridine;
6-(3-Fluoro-4-methoxyphenyl)-3-(2-methoxyphenyl)-[1,2,4]triazolo[4,3-a]pyridine;
6-(2,4-Dimethoxyphenyl)-3-(2-methoxyphenyl)-[1,2,4]triazolo[4,3-a]pyridine;

6-(4-Ethoxyphenyl)-3-(2-methoxyphenyl)-[1,2,4]triazolo[4,3-a]pyridine;
6-(4-Hydroxy-3-methylphenyl)-3-(2-methoxyphenyl)-[1,2,4]triazolo[4,3-a]pyridine;
6-(4-Amino-3-methoxyphenyl)-3-(2-methoxyphenyl)-[1,2,4]triazolo[4,3-a]pyridine;
6-(3-Amino-4-methylphenyl)-3-(2-methoxyphenyl)-[1,2,4]triazolo[4,3-a]pyridine;
6-(3-Aminophenyl)-3-(2-methoxyphenyl)-[1,2,4]triazolo[4,3-a]pyridine hydrochloride;
6-(3-Amino-4-methoxyphenyl)-3-(2-methoxyphenyl)-[1,2,4]triazolo[4,3-a]pyridine hydrochloride;
6-(4-Aminophenyl)-3-(2-methoxyphenyl)-[1,2,4]triazolo[4,3-a]pyridine hydrochloride;
6-(4-Methylaminophenyl)-3-(2-methoxyphenyl)-[1,2,4]triazolo[4,3-a]pyridine hydrochloride;
3-(4-Chloro-2-methoxyphenyl)-6-(3-fluoro-4-methoxyphenyl)-[1,2,4]triazolo[4,3-a]pyridine;
6-(3-Amino-4-methoxyphenyl)-3-(4-chloro-2-methoxyphenyl)-[1,2,4]triazolo[4,3-a]pyridine;
6-(3-Hydroxy-4-methoxyphenyl)-3-(2-methoxy-4-methylphenyl)-[1,2,4]triazolo[4,3-a]pyridine;
6-(3-Amino-4-methoxyphenyl)-3-(2-methoxy-4-methylphenyl)-[1,2,4]triazolo[4,3-a]pyridine;
6-(3-Fluoro-4-methoxyphenyl)-3-(2-methoxy-4-methylphenyl)-[1,2,4]triazolo[4,3-a]pyridine;
3-(2-Methoxyphenyl)-6-(4-methoxyphenyl)-7-methyl-[1,2,4]triazolo[4,3-a]pyridine;
3-(2-Methoxyphenyl)-6-(4-methoxyphenyl)-8-methyl-[1,2,4]triazolo[4,3-a]pyridine;
6-(4-Hydroxy-3-methoxyphenyl)-3-(2-methoxyphenyl)-[1,2,4]triazolo[4,3-a]pyridine;
3-(4-Chloro-2-methoxyphenyl)-6-(4-methoxyphenyl)-[1,2,4]triazolo[4,3-a]pyridine;
3-(4-Fluoro-2-methoxyphenyl)-6-(4-methoxyphenyl)-[1,2,4]triazolo[4,3-a]pyridine;
3-(4-Bromo-2-methoxyphenyl)-6-(4-methoxyphenyl)-[1,2,4]triazolo[4,3-a]pyridine;
3-(2-Methoxy-4-trifluoromethylphenyl)-6-(4-methoxyphenyl)-[1,2,4]triazolo[4,3-a]pyridine;
3-(2,6-Dimethoxyphenyl)-6-(4-methoxyphenyl)-[1,2,4]triazolo[4,3-a]pyridine;
3-(2,5-Dimethoxyphenyl)-6-(4-methoxyphenyl)-[1,2,4]triazolo[4,3-a]pyridine;
3-(6-Fluoro-2-methoxyphenyl)-6-(4-methoxyphenyl)-[1,2,4]triazolo[4,3-a]pyridine;
3,6-Bis(4-methoxyphenyl)-[1,2,4]triazolo[4,3-α]pyridine;
3-(3-Bromo-2,6-dimethoxyphenyl)-6-(4-methoxyphenyl)-[1,2,4]triazolo[4,3-a]pyridine;
3-(2-Methoxy-4-methylphenyl)-6-(4-methoxyphenyl)-[1,2,4]triazolo[4,3-a]pyridine;
6-(4-Methoxyphenyl)-3-phenyl-[1,2,4]triazolo[4,3-a]pyridine;
6-(4-Methoxyphenyl)-3-(2,4,5-trimethoxyphenyl)-[1,2,4]triazolo[4,3-a]pyridine;
3-(2,4-Dimethoxyphenyl)-6-(4-methoxyphenyl)-[1,2,4]triazolo[4,3-a]pyridine;
6-(4-Methoxyphenyl)-3-(2,3,4-trimethoxyphenyl)-[1,2,4]triazolo[4,3-a]pyridine;
3-(2,3-Dimethoxyphenyl)-6-(4-methoxyphenyl)-[1,2,4]triazolo[4,3-a]pyridine;
3-(2-Ethoxyphenyl)-6-(4-methoxyphenyl)-[1,2,4]triazolo[4,3-a]pyridine;
6-(4-Methoxyphenyl)-3-(2-methoxy-5-sulfamoylphenyl)-[1,2,4]triazolo[4,3-a]pyridine;
3-(2-Methoxy-5-methylphenyl)-6-(4-methoxyphenyl)-[1,2,4]triazolo[4,3-a]pyridine;
3-(3-Methoxyphenyl)-6-(4-methoxyphenyl)-[1,2,4]triazolo[4,3-a]pyridine;
6-(4-Methoxyphenyl)-3-(2-methylphenyl)-[1,2,4]triazolo[4,3-a]pyridine;
6-(4-methoxyphenyl)-3-(2-methylaminophenyl)-[1,2,4]triazolo[4,3-a]pyridine;
3-(2-dimethylaminophenyl)-6-(4-methoxyphenyl)-[1,2,4]triazolo[4,3-a]pyridine;
6-(3-Amino-4-methoxyphenyl)-3-(4-chloro-2-methoxyphenyl)-[1,2,4]triazolo[4,3-a]pyridine hydrochloride;
6-(3-Amino-4-methoxyphenyl)-3-(2-methoxy-4-methylphenyl)-[1,2,4]triazolo[4,3-a]pyridine hydrochloride;
3-(4-Chloro-2-methoxyphenyl)-6-(4-methoxyphenyl)-[1,2,4]triazolo[4,3-a]pyridine hydrochloride;
3-(2-Methoxy-4-methylphenyl)-6-(4-methoxyphenyl)-[1,2,4]triazolo[4,3-a]pyridine hydrochloride;
3-(4-Amino-2-methoxyphenyl)-6-(4-methoxyphenyl)-[1,2,4]triazolo[4,3-a]pyridine hydrochloride;
3-(4-Chloro-2-methoxyphenyl)-6-(4-methylaminophenyl)-[1,2,4]triazolo[4,3-a]pyridine;
3-(4-Chloro-2-methoxyphenyl)-6-(3-hydroxy-4-methoxyphenyl)-[1,2,4]triazolo[4,3-a]pyridine;
6-(3-Amino-4-methylphenyl)-3-(4-chloro-2-methoxyphenyl)-[1,2,4]triazolo[4,3-a]pyridine;
6-(3-Amino-4-methylphenyl)-3-(4-methyl-2-methoxyphenyl)-[1,2,4]triazolo[4,3-a]pyridine; and
6-(4-Methylaminophenyl)-3-(4-methyl-2-methoxyphenyl)-[1,2,4]triazolo[4,3-a]pyridine;
or a pharmaceutically acceptable salt thereof.

3. A method of treating a disorder responsive to the inhibition of uncontrolled cell proliferation in a mammal suffering therefrom, comprising administering to the mammal in need of such treatment an effective amount of a compound of claim 1, wherein said disorder is cancer.

4. The method according to claim 3, wherein said cancer is Hodgkin's disease, non-Hodgkin's lymphomas, acute or chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or pro static carcinoma.

5. The method of claim 3, wherein said cancer is drug resistant cancer.

6. The method of claim 3, further comprising administering at least one known anticancer agent, or a pharmaceutically acceptable salt of said agent.

7. The method according to claim 3, wherein said compound is administered together with at least one compound selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, campath, Herceptin®, Rituxan®, arsenic trioxide, gemcitabine, letrozole, fulvestrant, bendamustine, pralatrexate, pemetrexed, nelarabine, temozolomide, zoledronic acid, irinotecan, ixabepilone, cabazitaxel, vinorelbine, Panitumumab, Ofatumumab, Avastin, imatinib, gefitinib, erlotinib, lapatinib, sorafenib, sunitinib, nilotinib, dasatinib, pazopanib, bortezomib, vorinostat, romidepsin, temsirolimus, everolimus, thalidomide, lenalidomide, and alanosine.

8. The method of claim 3, further comprising treating said mammal with radiation-therapy.

9. The method of claim 3, wherein said compound is administered after surgical treatment of said mammal for said cancer.

10. A pharmaceutical composition comprising the compound of claim 1 and a pharmaceutically acceptable carrier.

11. The pharmaceutical composition of claim 10, further comprising at least one known anticancer agent, or a pharmaceutically acceptable salt of said agent.

12. The pharmaceutical composition of claim 10, further comprising at least one compound selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, campath, Herceptin®, Rituxan®, arsenic trioxide, gemcitabine, letrozole, fulvestrant, bendamustine, pralatrexate, pemetrexed, nelarabine, temozolomide, zoledronic acid, irinotecan, ixabepilone, cabazitaxel, vinorelbine, Panitumumab, Ofatumumab, Avastin, imatinib, gefitinib, erlotinib, lapatinib, sorafenib, sunitinib, nilotinib, dasatinib, pazopanib, bortezomib, vorinostat, romidepsin, temsirolimus, everolimus, thalidomide, lenalidomide, and alanosine.

13. The pharmaceutical composition of claim 12, comprising the compound of claim 4 and a pharmaceutically acceptable carrier.

14. The pharmaceutical composition of claim 12, comprising the compound of claim 5 and a pharmaceutically acceptable carrier.

15. The compound of claim 1, wherein $R_4$-$R_8$ independently are hydrogen, halo, $C_{1-6}$ alkoxy, $C_{1-10}$ alkyl, halo $C_{1-6}$ alkyl, hydroxy, secondary amino (—NHR), tertiary amino (—NRR); or aminosulfonyl; and wherein $R_9$-$R_{13}$ independently are hydrogen, halo, $C_{1-6}$ alkoxy, $C_{1-10}$ alkyl, halo $C_{1-6}$ alkyl, hydroxy, secondary amino (—NHR), tertiary amino (—NRR), or aminosulfonyl; wherein each R is independently $C_{1-6}$ alkyl.

16. The compound of claim 1, wherein $R_4$ and $R_5$, or $R_5$ and $R_6$, or $R_6$ and $R_7$, or $R_7$ and $R_8$, taken together with the atoms to which they are attached to form —OCH$_2$O— or —OCH$_2$CH$_2$O—.

17. The compound of claim 1, wherein $R_4$-$R_{13}$ independently are $C_{1-6}$alkoxy, hydroxy, secondary amino (—NHR), tertiary amino (—NRR), or aminosulfonyl; wherein each R is independently $C_{1-6}$ alkyl.

18. The compound of claim 1, wherein $R_4$-$R_{13}$ independently is $C_{1-6}$ alkoxy.

19. The compound of claim 1, wherein said compound is selected from the group consisting of:
    6-(4-Methoxy-3-methylphenyl)-3-(2-methoxyphenyl)-[1,2,4]triazolo[4,3-a]pyridine;
    6-(4-Dimethylaminophenyl)-3-(2-methoxyphenyl)-[1,2,4]triazolo[4,3-a]pyridine;
    6-(3-Hydroxy-4-methoxyphenyl)-3-(2-methoxyphenyl)-[1,2,4]triazolo[4,3-a]pyridine;
    6-(3-Chloro-4-methoxyphenyl)-3-(2-methoxyphenyl)-[1,2,4]triazolo[4,3-a]pyridine;
    6-(3-Amino-4-methoxyphenyl)-3-(2-methoxyphenyl)-[1,2,4]triazolo[4,3-a]pyridine hydrochloride;
    3-(4-chloro-2-methoxyphenyl)-6-(3-fluoro-2-methoxyphenyl)-[1,2,4]triazolo[4,3-a]pyridine;
    6-(3-Amino-4-methoxyphenyl)-3-(4-chloro-2-methoxyphenyl)-[1,2,4]triazolo[4,3-a]pyridine;
    6-(3-Hydroxy-4-methoxyphenyl)-3-(2-methoxy-4-methylphenyl)-[1,2,4]triazolo[4,3-a]pyridine;
    6-(3-Amino-4-methoxyphenyl)-3-(2-methoxy-4-methylphenyl)-[1,2,4]triazolo[4,3-a]pyridine;
    6-(3-Fluoro-4-methoxyphenyl)-3-(2-methoxy-4-methylphenyl)-[1,2,4]triazolo[4,3-a]pyridine;
    3-(4-Chloro-2-methoxyphenyl)-6-(4-methoxyphenyl)-[1,2,4]triazolo[4,3-a]pyridine;
    3-(4-Bromo-2-methoxyphenyl)-6-(4-methoxyphenyl)-[1,2,4]triazolo[4,3-a]pyridine;
    3-(2-Methoxy-4-methylphenyl)-6-(4-methoxyphenyl)-[1,2,4]triazolo[4,3-a]pyridine;
    3-(2,4-Dimethoxyphenyl)-6-(4-methoxyphenyl)-[1,2,4]triazolo[4,3-a]pyridine;
    3-(4-Chloro-2-methoxyphenyl)-6-(4-methylaminophenyl)-[1,2,4]triazolo[4,3-a]pyridine;
    3-(4-Chloro-2-methoxyphenyl)-6-(3-hydroxy-4-methoxyphenyl)-[1,2,4]triazolo[4,3-a]pyridine;
    6-(3-Amino-4-methylphenyl)-3-(4-chloro-2-methoxyphenyl)-[1,2,4]triazolo[4,3-a]pyridine;
    6-(3-Amino-4-methylphenyl)-3-(4-methyl-2-methoxyphenyl)-[1,2,4]triazolo[4,3-a]pyridine; and
    6-(4-Methylaminophenyl)-3-(4-methyl-2-methoxyphenyl)-[1,2,4]triazolo[4,3-a]pyridine;
    or a pharmaceutically acceptable salt thereof.

* * * * *

UNITED STATES PATENT AND TRADEMARK OFFICE
CERTIFICATE OF CORRECTION

PATENT NO. : 9,199,983 B2  
APPLICATION NO. : 13/885896  
DATED : December 1, 2015  
INVENTOR(S) : Cai et al.

Page 1 of 1

It is certified that error appears in the above-identified patent and that said Letters Patent is hereby corrected as shown below:

In the specification

Column 3
Line 34 please replace "or R7 and R5" with --or R7 and R8--

Column 18
Line 51 please replace "]trizolo[" with --]triazolo[--

Column 26
Line 43 please replace "prepared form" with --prepared from--

In the claims

Column 41
Line 48 please replace "[4,3-α]" with --[4,3-*a*]--

Column 42
Line 55 please replace "pro static" with --prostatic--

Column 43
Line 41 please replace "claim 4" with --claim 1--

Column 43
Line 44 please replace "claim 5" with --claim 2--

Signed and Sealed this
Twenty-eighth Day of June, 2016

Michelle K. Lee
*Director of the United States Patent and Trademark Office*